US006589185B1

(12) United States Patent
Archibald et al.

(10) Patent No.: US 6,589,185 B1
(45) Date of Patent: *Jul. 8, 2003

(54) METHOD AND APPARATUS FOR CALCULATING BLOOD PRESSURE OF AN ARTERY

(75) Inventors: G. Kent Archibald, Vadnais Heights, MN (US); Timothy G. Curran, Ramsey, MN (US); Orland H. Danielson, Roseville, MN (US); Marius O. Poliac, St. Paul, MN (US); Roger C. Thede, Afton, MN (US)

(73) Assignee: Medwave, Inc., Danvers, MA (US)

( * ) Notice: Subject to any disclaimer, the term of this patent is extended or adjusted under 35 U.S.C. 154(b) by 414 days.

This patent is subject to a terminal disclaimer.

(21) Appl. No.: 09/594,051

(22) Filed: Jun. 14, 2000

Related U.S. Application Data

(63) Continuation of application No. 09/070,311, filed on Apr. 30, 1998, now Pat. No. 6,099,477, which is a continuation of application No. 08/388,751, filed on Feb. 16, 1995, now Pat. No. 5,797,850, which is a continuation-in-part of application No. 08/227,506, filed on Apr. 14, 1994, now Pat. No. 5,450,852, which is a continuation-in-part of application No. 08/150,382, filed on Nov. 9, 1993, now abandoned.

(51) Int. Cl.[7] .................................................. A61B 5/02
(52) U.S. Cl. ....................................................... 600/494
(58) Field of Search .................................. 600/490–496, 600/500–503

(56) References Cited

U.S. PATENT DOCUMENTS

| 4,260,951 A | | 4/1981 | Lewyn |
| 4,307,727 A | | 12/1981 | Haynes |
| 4,461,266 A | | 7/1984 | Hood, Jr. et al. |
| 4,664,126 A | * | 5/1987 | Link .......................... 600/493 |
| 4,699,151 A | | 10/1987 | Link |
| 4,712,563 A | | 12/1987 | Link |
| 4,751,930 A | * | 6/1988 | Terada et al. ................ 600/494 |
| 4,799,491 A | | 1/1989 | Eckerle |
| 4,830,017 A | | 5/1989 | Perry et al. |
| 4,836,213 A | | 6/1989 | Wenzel et al. |
| 4,928,702 A | | 5/1990 | Cousin |
| 4,960,128 A | | 10/1990 | Gordon et al. |
| 4,984,577 A | | 1/1991 | Frankenreiter |
| 5,025,792 A | | 6/1991 | Hon et al. |
| 5,029,589 A | * | 7/1991 | Kato .......................... 600/490 |
| 5,033,471 A | | 7/1991 | Yokoe et al. |
| 5,163,438 A | | 11/1992 | Gordon et al. |
| 5,170,795 A | | 12/1992 | Ramsey, III et al. |
| 5,218,966 A | * | 6/1993 | Yamasawa ................... 600/480 |
| 5,218,967 A | * | 6/1993 | Shinomiya et al. ......... 600/493 |
| 5,238,000 A | | 8/1993 | Niwa |
| 5,240,007 A | * | 8/1993 | Pytel et al. .................. 600/485 |
| 5,247,944 A | | 9/1993 | Hirano et al. |
| 5,261,414 A | | 11/1993 | Aung et al. |
| 5,284,150 A | | 2/1994 | Butterfield et al. |
| 5,497,779 A | | 3/1996 | Takaya et al. |
| 5,797,850 A | * | 8/1998 | Archibald et al. .......... 600/494 |
| 5,941,828 A | * | 8/1999 | Archibald et al. .......... 600/494 |
| 6,099,477 A | * | 8/2000 | Archibald et al. .......... 600/494 |

* cited by examiner

*Primary Examiner*—Samuel G. Gilbert
(74) *Attorney, Agent, or Firm*—Kinney & Lange, P.A.

(57) ABSTRACT

The present invention is a method for calculating blood pressure of an artery having a pulse. The method includes applying a varying pressure to the artery. Pressure waveforms are sensed to produce pressure waveform data. Waveform parameters are derived from the sensed pressure waveform data. Blood pressure is then determined using the derived parameters.

19 Claims, 12 Drawing Sheets

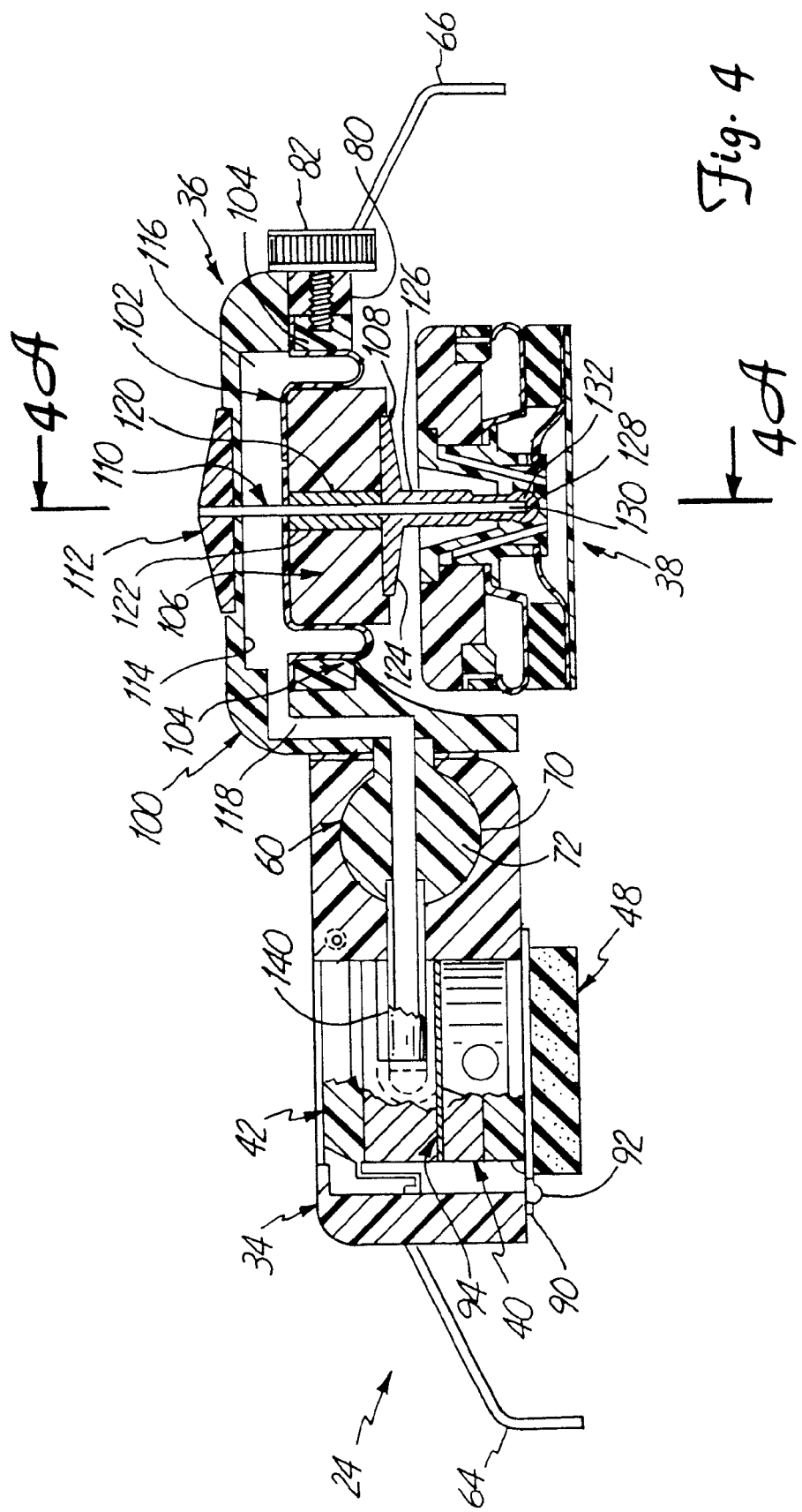

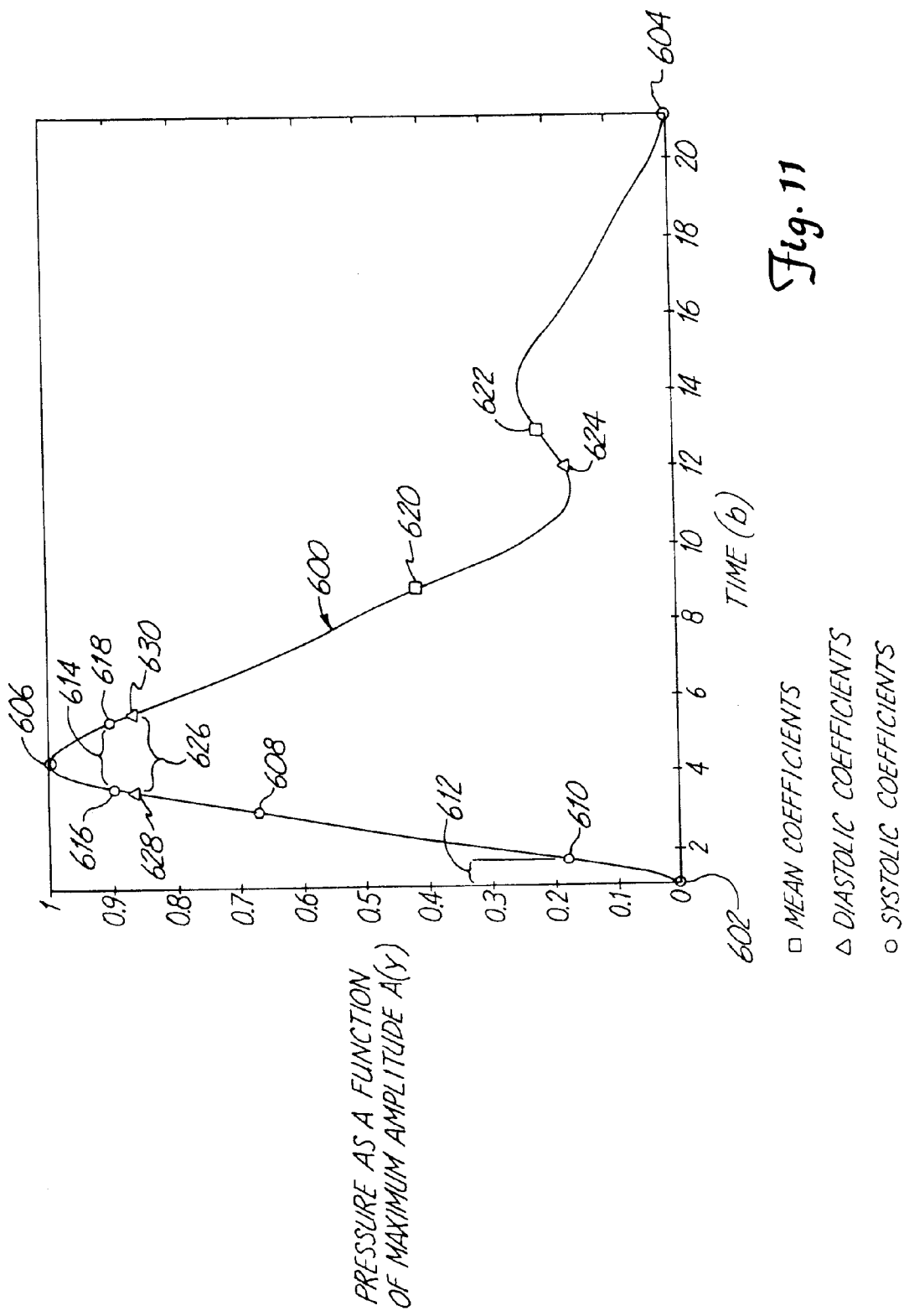

METHOD AND APPARATUS FOR CALCULATING BLOOD PRESSURE OF AN ARTERY

This is a continuation of application Ser. No. 09/070,311, filed Apr. 30, 1998, issued as U.S. Pat. No. 6,099,477, which is a continuation of application Ser. No. 08/388,751, filed Feb. 16, 1995, issued as U.S. Pat. No. 5,797,850, which is a continuation-in-part of application Ser. No. 08/227,506, filed Apr. 14, 1994, issued as U.S. Pat. No. 5,450,852 and entitled "CONTINUOUS NON-INVASIVE BLOOD MONITORING SYSTEM," which is a continuation-in-part of application Ser. No. 08/150,382, filed Nov. 9, 1993 entitled "CONTINUOUS NON-INVASIVE BLOOD PRESSURE MONITORING SYSTEM", abandoned.

BACKGROUND OF THE INVENTION

The present invention relates to systems for measuring arterial blood pressure. In particular, the invention relates to a method and apparatus for measuring arterial blood pressure in a relatively continuous and non-invasive manner.

Blood pressure has been typically measured by one of four basic methods: invasive, oscillometric, auscultatory and tonometric. The invasive method, otherwise known as an arterial line (A-Line), involves insertion of a needle into the artery. A transducer connected by a fluid column is used to determine exact arterial pressure. With proper instrumentation, systolic, mean and diastolic pressure may be determined. This method is difficult to set up, is expensive and involves medical risks. Set up of the invasive or A-line method poses problems. Resonance often occurs and causes significant errors. Also, if a blood clot forms on the end of the catheter, or the end of the catheter is located against the arterial wall, a large error may result. To eliminate or reduce these errors, the set up must be adjusted frequently. A skilled medical practitioner is required to insert the needle into the artery. This contributes to the expense of this method. Medical complications are also possible, such as infection or nerve damage.

The other methods of measuring blood pressure are non-invasive. The oscillometric method measures the amplitude of pressure oscillations in an inflated cuff. The cuff is placed against a cooperating artery of the patient and thereafter pressurized or inflated to a predetermined amount. The cuff is then deflated slowly and the pressure within the cuff is continually monitored. As the cuff is deflated, the pressure within the cuff exhibits a pressure versus time waveform. The waveform can be separated into two components, a decaying component and an oscillating component. The decaying component represents the mean of the cuff pressure while the oscillating component represents the cardiac cycle. The oscillating component is in the form of an envelope starting at zero when the cuff is inflated to a level beyond the patient's systolic blood pressure and then increasing to a peak value where the mean pressure of the cuff is equal to the patient's mean blood pressure. Once the envelope increases to a peak value, the envelope then decays as the cuff pressure continues to decrease.

Systolic blood pressure, mean blood pressure and diastolic blood pressure values can be obtained from the data obtained by monitoring the pressure within the cuff while the cuff is slowly deflated. The mean blood pressure value is the pressure on the decaying mean of the cuff pressure that corresponds in time to the peak of the envelope. Systolic blood pressure is generally estimated as the pressure on the decaying mean of the cuff prior to the peak of the envelope that corresponds in time to where the amplitude of the envelope is equal to a ratio of the peak amplitude. Generally, systolic blood pressure is the pressure on the decaying mean of the cuff prior to the peak of the envelope where the amplitude of the envelope is 0.57 to 0.45 of the peak amplitude. Similarly, diastolic blood pressure is the pressure on the decaying mean of the cuff after the peak of the envelope that corresponds in time to where the amplitude of the envelope is equal to a ratio of the peak amplitude. Generally, diastolic blood pressure is conventionally estimated as the pressure on the decaying mean of the cuff after the peak where the amplitude of the envelope is equal to 0.82 to 0.74 of the peak amplitude.

The auscultatory method also involves inflation of a cuff placed around a cooperating artery of the patient. Upon inflation of the cuff, the cuff is permitted to deflate. Systolic pressure is indicated when Korotkoff sounds begin to occur as the cuff is deflated. Diastolic pressure is indicated when the Korotkoff sounds become muffled or disappear. The auscultatory method can only be used to determine systolic and diastolic pressures.

Because both the oscillometric and the auscultatory methods require inflation of a cuff, performing frequent measurements is difficult. The frequency of measurement is limited by the time required to comfortably inflate the cuff and the time required to deflate the cuff as measurements are made. Because the cuff is inflated around a relatively large area surrounding the artery, inflation and deflation of the cuff is uncomfortable to the patient. As a result, the oscillometric and the auscultatory methods are not suitable for long periods of repetitive use.

Both the oscillometric and auscultatory methods lack accuracy and consistency for determining systolic and diastolic pressure values. The oscillometric method applies an arbitrary ratio to determine systolic and diastolic pressure values. As a result, the oscillometric method does not produce blood pressure values that agree with the more direct and generally more accurate blood pressure values obtained from the A-line method. Furthermore, because the signal from the cuff is very low compared to the mean pressure of the cuff, a small amount of noise can cause a large change in results and result in inaccurate measured blood pressure values. Similarly, the auscultatory method requires a judgment to be made as to when the Korotkoff sounds start and when they stop. This detection is made when the Korotkoff sound is at its very lowest. As a result, the auscultatory method is subject to inaccuracies due to low signal-to-noise ratio.

The fourth method used to determine arterial blood pressure has been tonometry. The tonometric method typically involves a transducer including an array of pressure sensitive elements positioned over a superficial artery. Hold down forces are applied to the transducer so as to flatten the wall of the underlying artery without occluding the artery. The pressure sensitive elements in the array typically have at least one dimension smaller than the lumen of the underlying artery in which blood pressure is measured. The transducer is positioned such that at least one of the individual pressure sensitive elements is over at least a portion of the underlying artery. The output from one of the pressure sensitive elements is selected for monitoring blood pressure. The pressure measured by the selected pressure sensitive element is dependent upon the hold down pressure used to press the transducer against the skin of the patient. These tonometric systems measure a reference pressure directly from the wrist and correlate this with arterial pressure. However, because the ratio of pressure outside the artery to the pressure inside the artery, known as gain, must be known and constant, tonometric systems are not reliable. Furthermore, if a patient moves, recalibration of the tonometric system is required because the system may experience a change in gains. Because the accuracy of these tonometric systems depends upon the accurate positioning of the individual pressure sensitive element over the underlying artery, placement of the transducer is critical. Consequently, placement of the transducer with these tonometric systems is time-consuming and prone to error.

The oscillometric, auscultatory and tonometric methods measure and detect blood pressure by sensing force or displacement caused by blood pressure pulses as the underlying artery is compressed or flattened. The blood pressure is sensed by measuring forces exerted by blood pressure pulses in a direction perpendicular to the underlying artery. However, with these methods, the blood pressure pulse also exerts forces parallel to the underlying artery as the blood pressure pulses cross the edges of the sensor which is pressed against the skin overlying the underlying artery of the patient. In particular, with the oscillometric and the auscultatory methods, parallel forces are exerted on the edges or sides of the cuff. With the tonometric method, parallel forces are exerted on the edges of the transducer. These parallel forces exerted upon the sensor by the blood pressure pulses create a pressure gradient across the pressure sensitive elements. This uneven pressure gradient creates at least two different pressures, one pressure at the edge of the pressure sensitive element and a second pressure directly beneath the pressure sensitive element. As a result, the oscillometric, auscultatory and tonometric methods produce inaccurate and inconsistent blood pressure measurements.

SUMMARY OF THE INVENTION

The present invention is an improved method for determining blood pressure of an artery having a pulse. As a varying pressure is applied to the artery, pressure waveforms are sensed to produce sensed pressure waveform data. The sensed pressure waveform data are then analyzed to derive waveform parameters. One or more blood pressure values are derived based upon the waveform parameters.

BRIEF DESCRIPTION OF THE DRAWINGS

FIG. 4 is a cross-sectional view of the wrist assembly.

FIG. 11 is a graph illustrating a corrected and scaled waveform taken from the waveforms of FIG. 9.

DETAILED DESCRIPTION OF THE PREFERRED EMBODIMENTS

I. Overview

Figure 1:
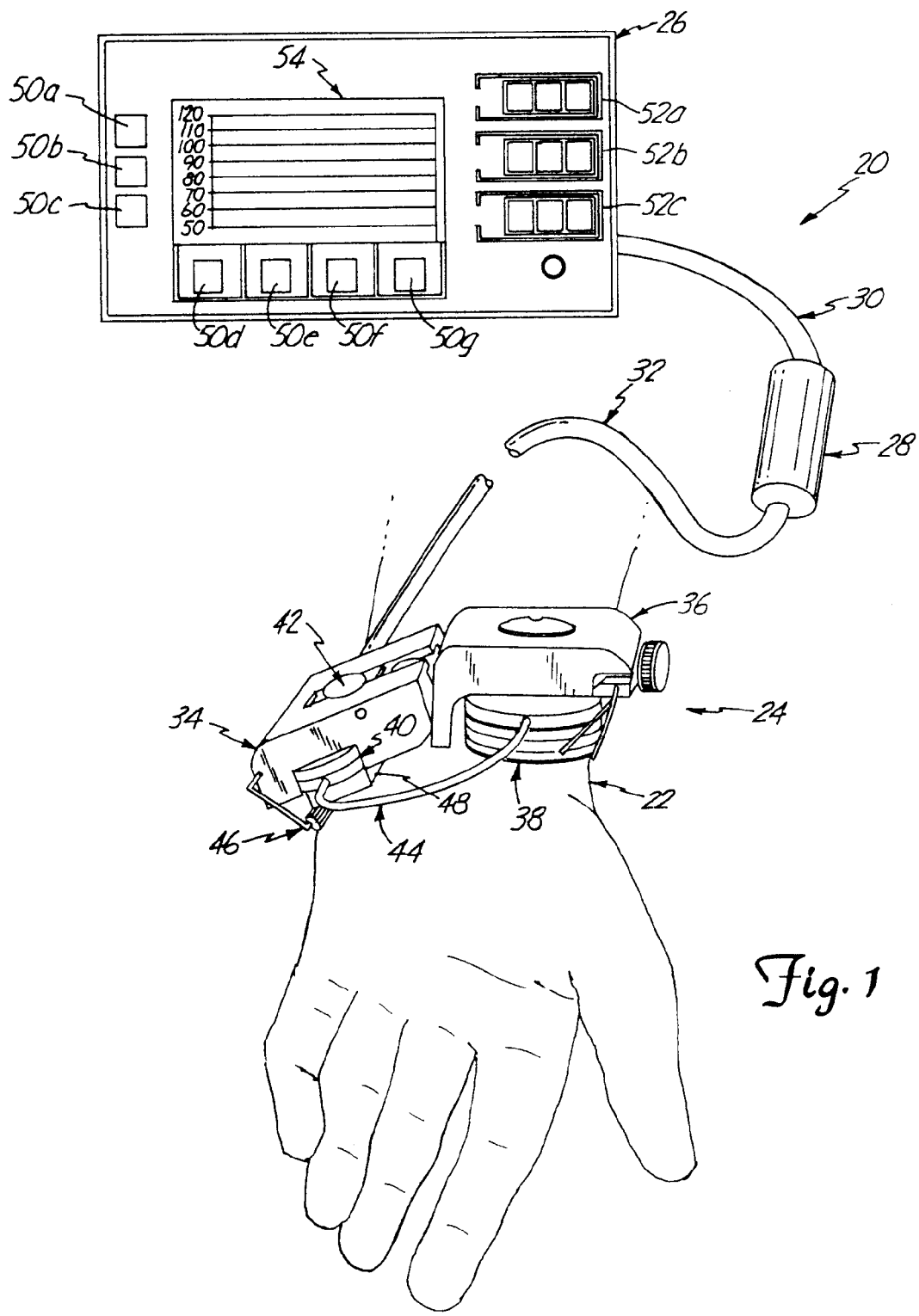
FIG. 1 is a perspective view of a blood pressure monitoring system having a sensor assembly mounted upon the wrist of a patient.

FIG. 1 illustrates blood pressure monitoring system 20 for measuring and displaying blood pressure within an underlying artery within wrist 22 of a patient. Monitoring system 20 includes wrist assembly 24, monitor 26, cylinder 28, cable 30 and cable 32.

Wrist assembly 24 is mounted on wrist 22 for applying a varying hold down pressure to an artery within wrist, and for sensing blood pressure waveforms produced in the artery. Wrist assembly 24 includes swivel mount 34, hold down assembly 36, sensor interface assembly 38, waveform pressure transducer 40, hold down pressure transducer 42, connection tube 44, wrist mount 46 and wrist pad 48.

Cylinder 28, under the control of monitor 26, supplies fluid pressure through cable 32 to wrist assembly 24 to produce the varying hold down pressure. Cylinder 28 includes a movable piston which is driven by stopper motor or linear actuator.

Electrical energization to wrist assembly 24 and pressure waveform sensor signals to monitor 26 are supplied over electrical conductors extending between monitor 26 and wrist assembly through cable 30, cylinder 28 and cable 32. Drive signals to cylinder 28 are supplied from monitor 26 through electrical conductors within cable 30.

Monitor 26 receives the pressure waveform sensor signals from wrist assembly 24, digitizes the signals to produce pressure waveform data for a plurality of beats, and performs waveform analysis on the data. The waveform analysis extracts a plurality of waveform parameters, which preferably include waveform shape, relative amplitude and gain parameters. From the waveform parameters, monitor 26 calculates or otherwise derives blood pressure values, such as mean blood pressure, diastolic blood pressure and systolic blood pressure. Monitor 26 then displays the derived blood pressure values.

As shown in FIG. 1, monitor 26 includes control switches or input keys 50a–50g, digital displays 52a–52c and display screen 54. Input keys 50a–50c comprise hard keys for controlling monitor 32. Input keys 50d–50g consist of software programmable keys which are adaptable for various functions. Digital displays 52a–52c continually display systolic, diastolic and mean blood pressure, respectively. Display screen 54 displays the blood pressure pulse waveforms and prompts to guide the operator.

In operation, sensor interface assembly 38 is positioned over the radial artery. Wrist mount 46 maintains the position of wrist assembly 24 including sensor interface assembly 38 on wrist 22. In response to fluid pressure supplied from cylinder 28 through cable 32, hold down assembly 36 applies force and moves sensor interface assembly 38 to vary the pressure applied to wrist 22 above the radial artery.

As this pressure is varied, distinct arterial pressure waveforms are exhibited by the blood pressure pulse within the underlying artery. Each waveform corresponds to a cardiac cycle. Each arterial pressure waveform or shape is obtained by sensing and measuring pressures exhibited by the pulse of the underlying artery versus time during an individual cardiac cycle. Arterial pressure applied to sensor interface assembly 38 and is transferred as a fluid pressure from interface assembly 38 to waveform pressure transducer 40 through tube 44. The electrical sensor signals from transducer 40 are supplied to monitor 26 for digitization and analysis.

The amplitude of each sensed waveform is a function of the applied pressure applied to the artery by sensor interface assembly 38 and the amplitude of the arterial pulse. The shape characteristics of at least one waveform and other parameters derived from the sensed waveforms are used by digital signal processing circuitry of monitor 26 to determine systolic, mean and diastolic pressure. The calculated pressures are displayed by displays 52a–52c and display screen 54.

II. Wrist Assembly 24

Wrist assembly 24 is shown in further detail in FIGS. 2–6. Swivel mount 34 and hold down assembly 36 are side-by-side, and are pivotally connected by swivel joint 60. Swivel mount 34 carries transducers 40 and 42 and wrist pad 48. Sensor interface assembly 38 is pivotally connected to and is positioned below hold down assembly 36. Wrist mount 46, which includes flexible wrist band 62 and wire loops 64 and 66, is connected between an outer end of swivel mount 34 and teeter mount 68 at an opposite outer end of hold down assembly 36.

Figure 2:
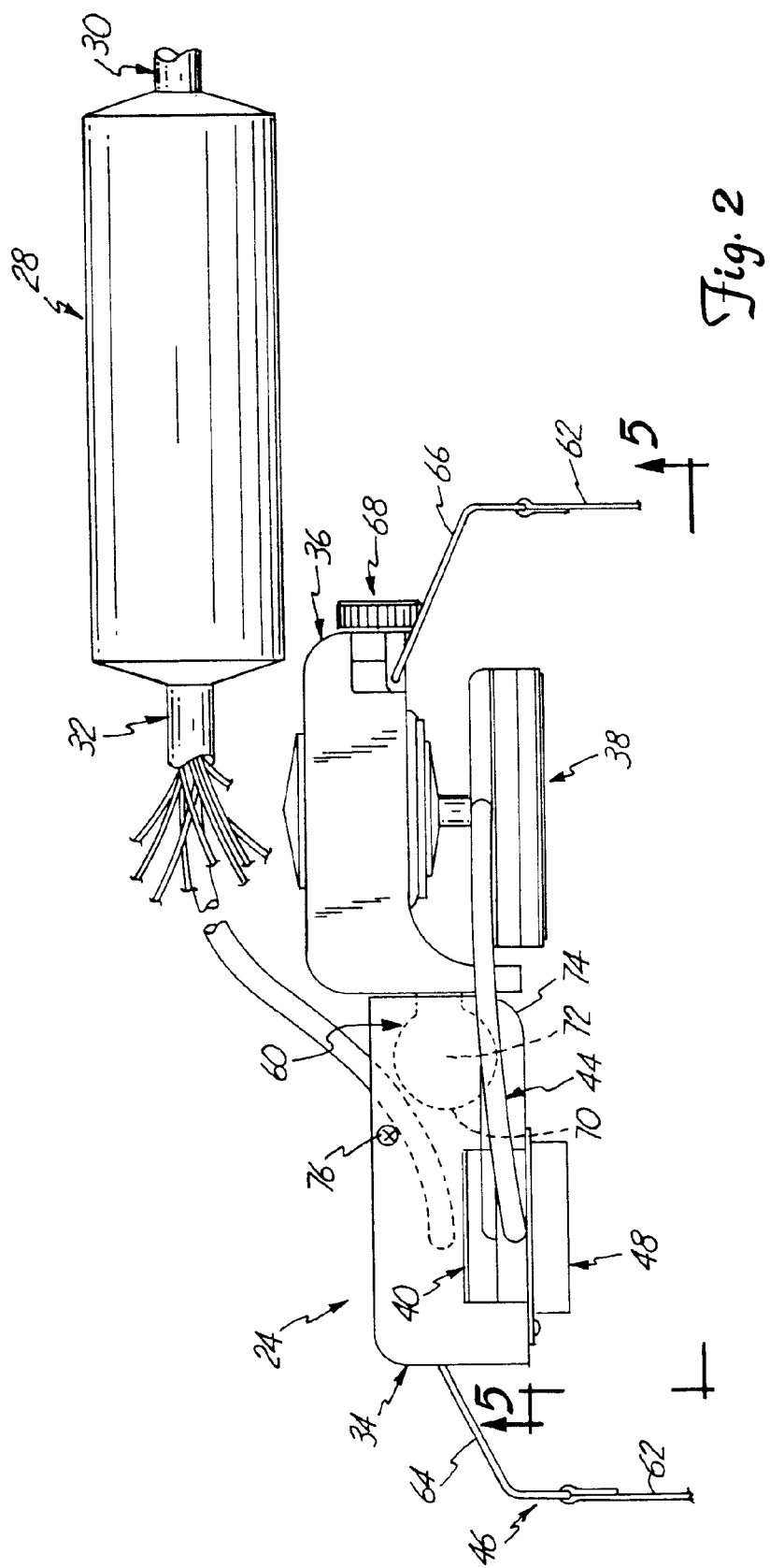
FIG. 2 is a side view of the wrist assembly of the blood pressure monitoring system of FIG. 1.

FIG. 2 is a side elevational view illustrating wrist assembly 24 in greater detail. Swivel mount 34 is a U-shaped body. Swivel joint 60 is formed by a socket 70 of swivel mount 34 and swivel ball 72 of hold down assembly 36. Socket 70 extends into a channel within the U-shaped configuration of swivel mount 34 and is sized for receiving swivel ball 72 which projects from an inner end wall of hold down assembly 36. The ball socket swivel joint provided by ball 72 and socket 70 permit swivel mount 34 and hold down assembly 36 to rotate and pivot in virtually any direction so as to better conform to wrist 22. To aid in pivoting swivel mount 34 with respect to hold down assembly 36, swivel mount 34 includes an arcuate or beveled lower edge 74 along its inner end. Beveled edge 74 permits hold down assembly 36 to pivot downward so as to wrap around wrist 22 (or alternate anatomy) of a patient.

Swivel mount 34 further includes a tightening screw 76 which extends across swivel mount 34 adjacent socket 70 and ball 72. Tightening screw 76 permits socket 70 of swivel mount 34 to be tightened about ball 72 so as to increase friction between socket 70 and ball 72 to adjust the level of force necessary to readjust the positioning of swivel mount 34 and hold down assembly 36. Untightening screw 76 permits ball 72 to be released from socket 70 such that hold down assembly 36 and sensor interface assembly 38 may be disassembled from swivel mount 34.

Figure 3:
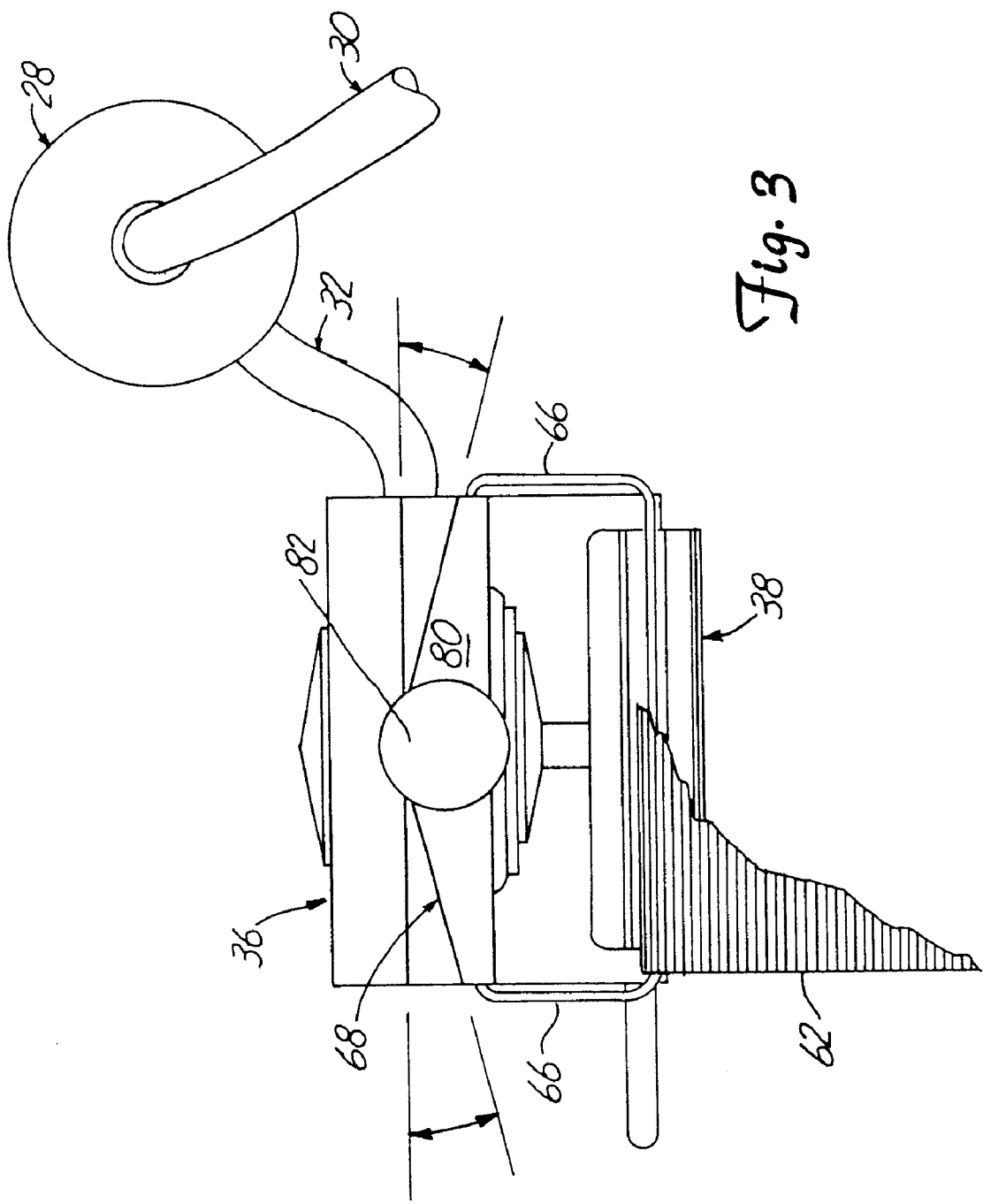
FIG. 3 is an end view of the wrist assembly.

FIG. 3 is a end elevational view of blood pressure monitoring system 20 of FIG. 1, illustrating teeter mount 68 in greater detail. As shown by FIG. 3, teeter mount 68 includes fulcrum 80 and tightening screw 82. Fulcrum 80 is generally a triangular shaped member having two opposing slanted top surfaces. Fulcrum 80 is coupled to loop 66 and thereby to wrist band 62. Fulcrum 80 teeters about hold down assembly 36 and permits loop 66 and wrist band 62 to be adjustably positioned so as to better conform to wrist 22. Tightening screw 82 extends through fulcrum 80 and threadably engages hold down assembly 36. Tightening screw 82 tightens fulcrum 80 against hold down assembly 36 so that the position of fulcrum 80 may be frictionally set. In FIG. 3, fulcrum 80 is shown in a middle position, and can be rotated either a clockwise or counterclockwise direction as needed.

Wrist assembly 24 stably and securely positions sensor interface assembly 38 over the underlying artery of the patient. Swivel mount 34 may be rotated and pivoted in practically all directions about socket 70 and ball 72. Furthermore, teeter mount 68 permits wrist band 62 to be teetered or adjusted so as to better conform with wrist 22 of the patient. Wrist band 62 wraps around wrist 22 to secure sensor interface assembly 38 and wrist pad 48 adjacent wrist 22 of the patient. Because sensor interface assembly 38 is more securely and stably positioned above the underlying artery of wrist 22, patient movement is less likely to reposition sensor interface assembly 38. As a result, sensor interface assembly 38 can be reliably located over the underlying artery so that more accurate and consistent blood pressure measurements may be taken.

As shown in FIG. 4, swivel mount 34 carries waveform pressure transducer 40, hold down pressure transducer 42, and wrist pad 48. Waveform pressure transducer 40 senses blood pressure waveforms from the artery which is transmitted to transducer 40 from sensor interface assembly 38 through fluid tube 44 (FIG. 1). Hold down pressure transducer 42 senses fluid pressure supplied by cylinder 28 to hold down assembly 36, and is used as a safety feature to detect an excess hold down pressure condition. Wrist pad 48 is preferably adhesively secured to plate 90 at a bottom surface of swivel mount 34. Pad 48 is preferably made of a soft flexible and compressible material so that swivel mount 34 better conforms to the wrist of a patient. Plate 90 is preferably made of a metal such as brass and is screwed to swivel mount 34 by screw 92. Conductive plate 94 is secured within swivel mount 34 and is spaced from plate 90 so that transducer 40 is positioned between plates 90 and 94. Transducer 40 preferably has a metallic conductive surface such as brass which contacts conductive plate 94, which is electrically grounded. As a result, brass plate 94 electrically grounds transducer 40 so as to drain static charge from transducer 40.

As shown by FIG. 4, hold down pressure assembly 36 includes swivel ball 72, housing 100, diaphragm 102, ring 104, piston 106, piston rod 108, pin 110 and pin mount 112. Diaphragm 102 comprises a generally circular sheet of flexible material such as reinforced rubber. Diaphragm 102 is spaced from and cooperates with interior cavity 114 formed within housing 100 to define pressure chamber 116. Pressure chamber 116 extends generally above and partially around piston 106. Pressure chamber 116 receives pressurized fluid from cylinder 28 through fluid passage 118 such that diaphragm 102 expands and contracts to drive piston 106 and piston rod 108 up and down. As a result, a selected pressure may be applied to piston 106 and piston rod 108 so as to selectively apply a pressure to sensor interface assembly 38, which is pivotally mounted to the lower end of piston rod 108. By varying the volume of fluid within pressure chamber 116, blood pressure monitoring system 20 applies a varying hold down pressure to sensor interface assembly 38 and the underlying artery.

Diaphragm 102 is supported in place by ring 104. Ring 104 encircles the outer perimeter of diaphragm 102 and captures an outer perimeter or edge portion of diaphragm 102 between ring 104 and housing 100 so as to seal diaphragm 102 against housing 100. Ring 104 is preferably adhesively secured to housing 100 and diaphragm 102.

Piston 106 is preferably a disk or cylinder shaped member which has its top surface preferably fixedly coupled (such as by an adhesive) to diaphragm 102. Consequently, as fluid is supplied to chamber 116, the volume of chamber 116 expands by moving piston 106 downward. Bore 120 extends from top to bottom of piston 106 and is sized for receiving a portion of piston rod 108. Piston 106 mates with piston rod 108 and exerts pressure upon piston rod 108 and sensor interface assembly 38.

Piston rod 108 is coupled to piston 106 and sensor interface assembly 38. Piston rod 108 includes plug 122, flange 124, stem 126, ball 128 and pin hole 130. Plug 122 is cylindrically shaped and is press fit within bore 120 to secure piston rod 108 to piston 106. Flange 124 projects outwardly from plug 122 and fits within a depression formed in the bottom surface of piston 106. As a result, piston 106 presses against flange 124 of piston rod 108 to drive piston rod 108. Alternatively, because piston rod 108 is secured to piston 106 by plug 122, piston 106 lifts piston rod 108 as pressure is decreased within pressure chamber 116. Stem 126 integrally extends downward from flange 124 and has a length extending into interface assembly 38. Ball 128 is integrally formed at the lower end of stem 126 and is received within socket 132 of sensor interface assembly 38. As a result, sensor interface assembly 38 pivots about ball 128 of piston rod 108.

Pin hole 130 axially extends through piston rod 108 and is sized for receiving pin 110. Pin 110 is fixedly secured to housing 100 by pin mount 112 and extends through housing 100 into pin hole 130. Pin 110 has a diameter smaller than the diameter of pin hole 130 and extends into stem 126. Pin 110 guides the up and down movement of piston 106 and piston rod 108 as pressure within pressure chamber 116 is varied. Pin 110 prevents lateral movement of piston 106 and piston rod 108 so that piston 106 and piston rod 108 apply only a perpendicular force to sensor interface assembly 38. As a result, pin 110 permits piston 106 and piston rod 108 to move up and down while pin 110 remains fixedly supported by pin mount cap 112 to housing 100. Pin 110 is preferably made from a hard rigid material such as stainless steel.

Figure 4A:
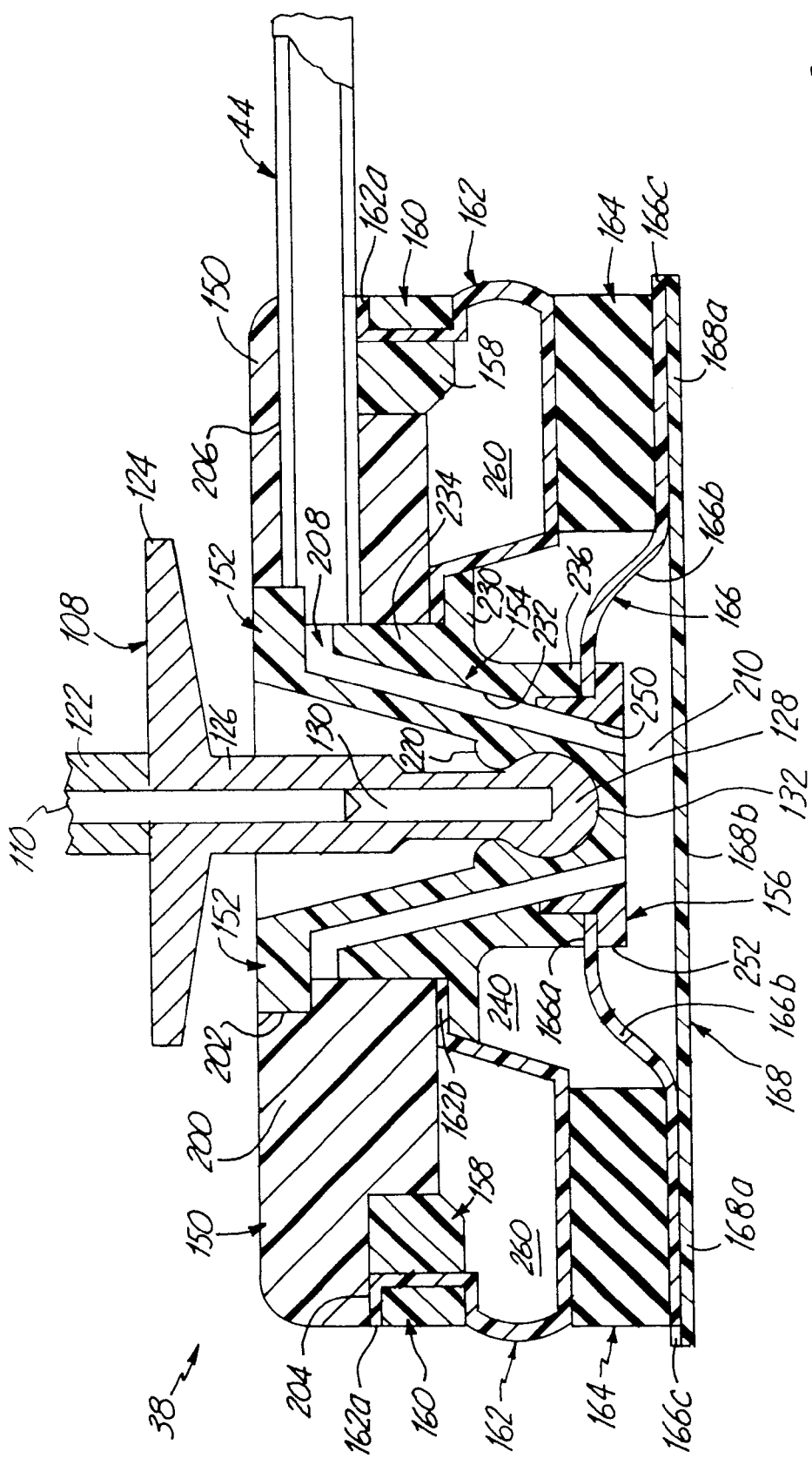
FIG. 4A is an expanded cross-sectional view of the sensor interface along section 4A—4A of FIG. 4.
Figure 5:
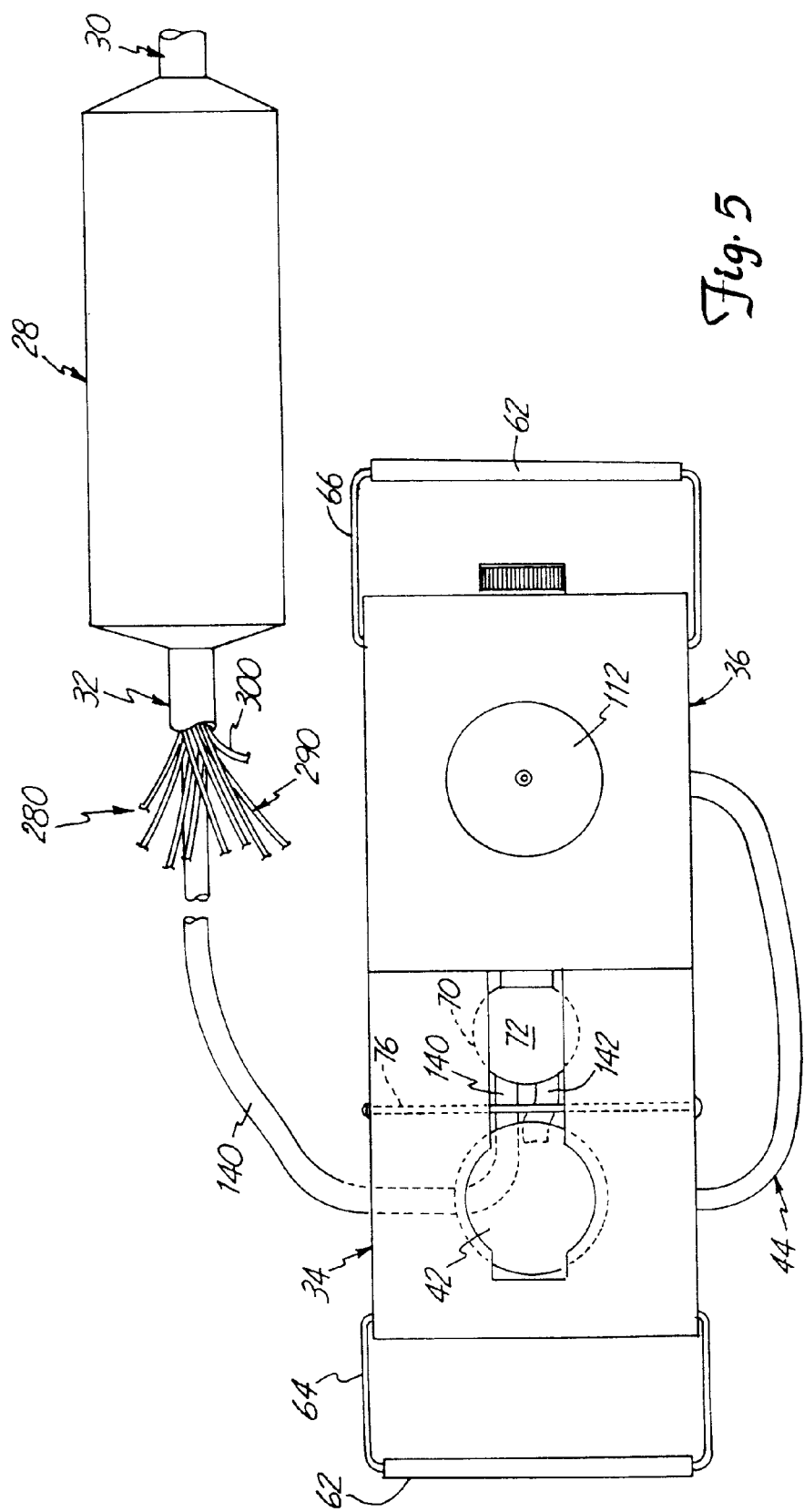
FIG. 5 is a top view of the wrist assembly and cylinder of the system of FIG. 1.
Figure 6:
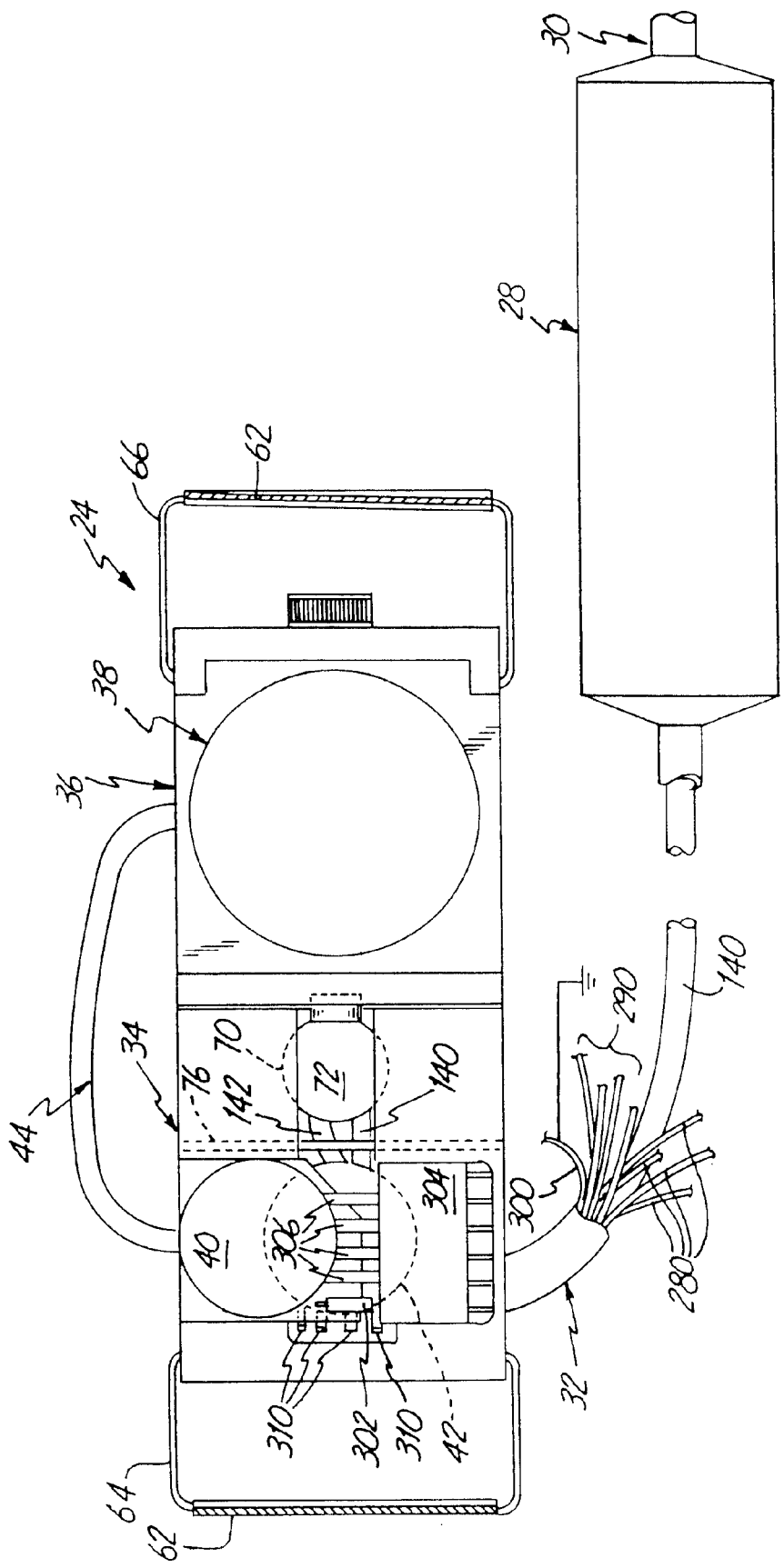
FIG. 6 is a bottom view of the wrist assembly and cylinder with a portion removed.

As shown by FIG. 4, hold down pressure assembly 28 further includes pressure supply passage 118, which extends from pressure chamber 116 through swivel ball 72 where it connects with flexible tubes 140 and 142 (shown in FIGS. 5 and 6). Flexible tube 140 extends through cable 32 from cylinder 28 to passage 118 in swivel ball 72. Flexible tube 142 connects passage 118 to transducer 42 in swivel mount 34. This allows transducer to monitor the fluid pressure in chamber 116. Fluid supply tube 140 applies pressurized fluid from cylinder 28 into pressure chamber 116 to vary the pressure within chamber 116 so as to drive piston 106 and piston rod 108.

FIGS. 4 and 4A illustrate sensor interface assembly 38 in detail. FIG. 4 is a cross-sectional view of wrist assembly 24. FIG. 4A is an enlarged cross-sectional view of sensor interface assembly 38, taken along section 4A—4A of FIG. 4. Sensor interface assembly 38 includes top plate 150, upper V mount 152, lower V mount 154, diaphragm lock 156, inner mounting ring 158, outer mounting ring 160, side wall diaphragm 162, damping ring 164, inner diaphragm 166 and outer diaphragm 168.

Top plate 150 is a generally flat annular platform having a central bore 200, shoulder 202, shoulder 204, and side bore 206. Central bore 200 receives and holds lower V mount 154. Upper V mount 152 engages shoulder 202 and extends downward into bore 200 and into lower V mount 154. Rings 158 and 160 and the upper outer end of side wall diaphragm 162 are mounted in shoulder 204.

Side bore 206 is defined within top 150 and extends through top 150 so as to be in communication with fluid passage 208 defined between upper and lower V mounts 152 and 154 and between upper V mount 152 and diaphragm lock 156. Side bore 206 receives an end of tube 44 so that tube 44 is in fluid communication with fluid passage 208 and sensor interface chamber 210 (which is defined by diaphragms 166 and 168). Fluid passage 208 and tube 44 provide fluid communication between sensor interface chamber 210 and transducer 40 eccentric to socket 132. As a result, piston rod 108 may be pivotally connected to sensor interface assembly 38 at a lower pivot point.

Upper V mount 152 is a funnel-shaped socket which is sized for receiving the lower or distal end of piston rod 108. Preferably, upper V mount 152 extends through central bore 200 of top plate 150 to a location near sensor interface chamber 210. Upper V mount 152 is fixedly secured to an upper portion of top plate at shoulder 202. Upper V mount 152 is supported by top plate 150 such that upper V mount 152 is spaced from lower V mount 154 to define annular fluid passage 208. Fluid passage 208 is in fluid communication with an sensor interface chamber 210. A fluid coupling medium fills chamber 210, passage 208 and tube 44 all the way to transducer 40. Upper V mount 152, which is made from a material such as nylon and forms detent 220 and socket 132 for pivotally receiving a ball member 128 of piston rod 108. As a result, sensor interface assembly 38 may be pivoted about socket 132 so as to better conform to the anatomy of the patient. Furthermore, because socket 132 is adjacent to sensor interface chamber 210, sensor interface assembly 38 is pivotally coupled to piston rod 108 about a low pivot point. This permits sensor interface assembly 38 to be stably positioned above the underlying artery. In addition, the low pivot point enables hold down assembly 36 to apply a more direct, uniform force on diaphragm 168. Thus, the hold down pressure applied by hold down pressure assembly 36 is more uniformly applied to the anatomy of the patient above the underlying artery.

Lower V mount 154 is a generally cylindrical shaped member including step or spar 230 and bore 232. An outer surface or perimeter of lower V mount 154 projects outwardly to form spar 230. Spar 230 engages the lower surface of top plate 150 to partially support side wall diaphragm 162 which is partially captured between top plate 150 and spar 230. In the preferred embodiment, adhesive is used between the lower surface of top plate 150 and spar 230 to fixedly secure the portion of side wall diaphragm 162 trapped therebetween. Alternatively, spar 230 may be press fit against the lower surface of top plate 150 to secure and support side wall diaphragm 162. Spar 230 further divides the outer perimeter of lower V mount 154 into two portions, an upper portion 234 and a lower portion 236. Upper portion 234 fits within bore 200 of top plate 150. Upper portion 234 is preferably adhesively secured to top plate 150 within bore 200. Lower portion 236 extends below spar 230. Lower portion 236, spar 230 and side wall diaphragm 162 define expansion cavity 240. Expansion cavity 240 enables upper diaphragm 166 to initially change shape while only experiencing a small change in volume.

Diaphragm lock 156 is a thin, elongated, annular ring including bore 250 and lower lip 252. Bore 250 extends through diaphragm lock 156 and with upper V mount 152, defines a portion of fluid passage 208. Lip 252 projects outwardly from a lower end of diaphragm lock 156. Diaphragm lock 156 fits within bore 232 of lower V mount 154 until an inner edge of diaphragm lock 156 is captured between inserts, lip 252 and the lower end of lower V mount 154. Diaphragm lock 156 is preferably adhesively affixed to lower V mount 154. Alternatively, diaphragm lock 156 may be press fit within lower V mount 154.

Side wall diaphragm 162, rings 158 and 160 and top plate 150 define an annular deformable chamber 260 coupled between top plate 150 and ring 164. Side wall diaphragm 162 is preferably formed from a generally circular sheet of flexible material, such as vinyl, and is partially filled with fluid. Diaphragm 162 has a hole sized to fit around upper portion 234 of lower V mount 154. Diaphragm 162 includes outer edge portion 162a and inner edge portion 162b. Outer edge portion 162a is trapped and held between outer ring 160 and top plate 150. Inner edge portion 162b is trapped and supported between top plate 150 and spar 230 of lower V mount 154. Diaphragm 162 is made from a flexible material and is bulged outward when chamber 260 is partially filled with fluid. Chamber 260 is compressible and expandable in the vertical direction so as to be able to conform to the anatomy of the patient surrounding the underlying artery. As a result, the distance between top plate 150 and the patient's anatomy can vary around the periphery of side wall diaphragm 162 according to the contour of the patient's anatomy. Furthermore, because fluid is permitted to flow through and around chamber 260, pressure is equalized around the patient's anatomy.

Damping ring 164 generally consists of an annular compressible ring and is preferably formed from a foam rubber or other pulse dampening material such as open celled foam or closed cell foam. Ring 164 is centered about and positioned between side wall diaphragm 162 and diaphragms 166 and 168. Damping ring 164 is isolated from the fluid coupling medium within chamber 210. Because ring 164 is formed from a compressible material, ring 164 absorbs and a dampens forces in a direction parallel to the underlying artery which are exerted by the blood pressure pulses on sensor interface assembly 38 as the blood pressure pulse crosses sensor interface assembly 38. Because bottom ring 164 is isolated from the fluid coupling medium, the forces absorbed or received by ring 164 cannot be transmitted to the fluid coupling medium. Instead, these forces are transmitted across ring 164 and side wall diaphragm 162 to top plate 150. Because this path is distinct and separate from the fluid coupling medium, chamber 210 and the fluid coupling medium are isolated from these forces. In addition, ring 164 also presses tissue surrounding the artery to neutralize or offset forces exerted by the tissue.

Upper diaphragm 166 is an annular sheet of flexible material having an inner portion 166a, an intermediate portion 166b, an outer portion 166c and an inner diameter sized to fit around diaphragm lock 156. Inner portion 166a is trapped or captured between lip 252 of diaphragm lock 156 and the bottom rim of lower V mount 154. Inner portion 166A is preferably adhesively affixed between lip 252 and lower V mount 154.

Intermediate portion 166b lies between inner portion 166a and outer portion 166c. Intermediate portion 166b is adjacent to expansion cavity 240 and is isolated from ring 164 and chamber 260. Because intermediate portion 166b is positioned adjacent to expansion cavity 240, intermediate portion 166b is permitted to initially move upward into expansion cavity 240 as chamber 260, ring 164 and outer diaphragm 168 conform to the anatomy of the patient surrounding the underlying artery while the experiences only a small change in volume. As ring 164 is pressed against the anatomy of the patient surrounding the artery to neutralize or offset forces exerted by the tissue, diaphragm 168 is also compressed. However, because intermediate portion 166b is permitted to roll into expansion cavity 240, chamber 210 does not experience a large volume decrease and a large corresponding pressure increase. Thus, sensor interface assembly 38 permits greater force to be applied to the anatomy of the patient through ring 164 to neutralize tissue surrounding the artery without causing a corresponding large change in pressure within chamber 210 as the height of the side wall changes. As a result, sensor interface assembly 38 achieves more consistent and accurate blood pressure measurements.

Outer diaphragm 168 is a generally circular sheet of flexible material capable of transmitting forces from an outer surface to fluid within chamber 210. Outer diaphragm 168 is coupled to inner diaphragm 166 and is configured for being positioned over the anatomy of the patient above the underlying artery. Outer diaphragm sheet 168 includes non-active portion or skirt 168a and active portion 168b. Skirt 168a constitutes the area of diaphragm 168 where inner diaphragm 166, namely outer portion 166c, is bonded to outer diaphragm 168. Skirt 168a and outer portion 166c are generally two bonded sheets of flexible material, forces parallel to the underlying artery are transmitted across skirt 168a and outer portion 166c and are dampened by the compressible material of ring 164.

Active portion 168b is constituted by the portion of outer diaphragm sheet 168 which is not bonded to inner diaphragm 166. Active portion 168b is positioned below and within the inner diameter of ring 164. Active portion 168b is the active area of sensor interface assembly 38 which receives and transmits pulse pressure to transducer 40. Active portion 168b of diaphragm 168, intermediate portion 166b of diaphragm 166 and diaphragm lock 156 define sensor interface chamber 210.

The coupling medium within chamber 210 may consist of any fluid (gas or liquid) capable of transmitting pressure from diaphragm 168 to transducer 40. The fluid coupling medium interfaces between active portion 168b of diaphragm 168 and transducer 40 to transmit blood pressure pulses to transducer 40. Because the fluid coupling medium is contained within sensor interface chamber 210, which is isolated from the side wall of sensor interface assembly 38, the fluid coupling medium does not transmit blood pressure pulses parallel to the underlying artery, forces from the tissue surrounding the underlying artery and other forces absorbed by the side wall to transducer 40. As a result, sensor interface assembly 38 more accurately measures and detects arterial blood pressure.

Sensor interface assembly 38 provides continuous external measurements of blood pressure in an underlying artery. Because sensor interface assembly 38 senses blood pressure non-invasively, blood pressure is measured at a lower cost and without medical risks. Because sensor interface assembly 38 is relatively small compared to the larger cuffs used with oscillometric and auscultatory methods, sensor interface assembly 38 applies a hold down pressure to only a relatively small area above the underlying artery of the patient. Consequently, blood pressure measurements may be taken with less discomfort to the patient. Because sensor interface assembly 38 does not require inflation or deflation, continuous, more frequent measurements may be taken.

Furthermore, sensor interface assembly 38 better conforms to the anatomy of the patient so as to be more comfortable to the patient and so as to achieve more consistent and accurate blood pressure measurements. Because chamber 260 is deformable and partially filled with fluid, chamber 260 better conforms to the anatomy of the patient and equalizes pressure applied to the patient's anatomy. Because ring 164 is compressible and because diaphragm 168 is flexible and is permitted to bow or deform inwardly, ring 164 and diaphragm 168 also better conform to the anatomy of the patient. At the same time, however, sensor interface assembly 38 does not experience a large sudden increase in pressure in sensor interface chamber 210 as ring 164 and diaphragm 168 are pressed against the anatomy of the patient. Chamber 260 and ring 164 apply force to the anatomy of the patient to neutralize the forces exerted by tissue surrounding the underlying artery. Because chamber 260 and ring 164 are both compressible, the height of the side wall decreases as side wall is pressed against the patient. Diaphragms 166 and 168 are also conformable. However, because intermediate portion 166b of inner diaphragm 166 is permitted to move upward into expansion cavity 240, sensor interface chamber 210 does not experience a large volume decrease and a corresponding large pressure increase. Thus, the side wall is able to apply a greater force to the anatomy of the patient without causing a corresponding large, error producing increase in pressure within sensor interface chamber 210 due to the change in height of the side wall and the change in shape of outer diaphragm 168.

At the same time, sensor interface assembly 38 permits accurate and consistent calculation of blood pressure. Because of the large sensing area through which blood pressure pulses may be transmitted to transducer 40, sensor interface assembly 38 is not as dependent upon accurate positioning of active portion 168b over the underlying artery. Thus, sensor interface assembly 38 is more tolerant to patient movement as measurements are being taken.

Moreover, sensor interface assembly 38 achieves a zero pressure gradient across the active face or portion 168b of the sensor, achieves a zero pressure gradient between the transducer and the underlying artery, attenuates or dampens pressure pulses that are parallel to the sensing surface of the sensor, and neutralizes forces of the tissue surrounding the underlying artery. Sensor interface assembly 38 contacts and applies force to the anatomy of the patient across skirt 168a and active portion 168b. However, the pressure within interface chamber 210 is substantially equal to the pressure applied across active portion 168b. The remaining force applied by sensor interface assembly 38 across skirt 168a which neutralizes or offsets forces exerted by the tissue surrounding the underlying artery is transferred through the side wall (ring 164 and chamber 260) to top plate 150. As a result, the geometry and construction of sensor interface assembly 38 provides the proper ratio of pressures between skirt 168a and active portion 168b to neutralize tissue surrounding the underlying artery and to accurately measure the blood pressure of the artery. In addition, because the fluid coupling medium within sensor interface chamber 210 is isolated from the side wall, pressure pulses parallel to the underlying artery, forces from tissue surrounding the underlying artery and other forces absorbed by the side wall are not transmitted through the fluid coupling medium to transducer 40. Consequently, sensor interface assembly 38 also achieves a zero pressure gradient between transducer 40 and the underlying artery.

FIG. 5 is a top view of wrist assembly 24. FIG. 5 further illustrates portions of swivel mount 34 and cable 30 in greater detail. Fluid tube 140 has one end connected to passage 118 in swivel ball 72 and its other end connected to cylinder 28.

Fluid tube 142 extends between transducer 42 and passage 118 in ball 72. Fluid tube 142 fluidly connects pressure chamber 116 and transducer 42. As a result, transducer 42 senses the pressure within pressure chamber 116. Transducer 42 produces electrical signals representing the sensed hold down pressure within pressure chamber 116. These electrical signals are transmitted by electrical wires 280 which extend within cables 30 and 32 to monitor 26 (shown in FIG. 1). As a result, monitor 26 may continuously verify that the actual pressure within pressure chamber 116 is within a safe range.

As further shown by FIG. 5, cable 32 additionally encloses electrical wires 290 from transducer 40 (shown in FIG. 4). Electrical wires 290 transmit electrical signals representing blood pressure amplitudes sensed by transducer 40. Cable 32 also encloses an electrical grounding wire 300 which is electrically connected through resistor 302 (FIG. 6) to brass plate 94 (shown in FIG. 4) and which electrically grounds transducers 40 and 42.

FIG. 6 is a bottom view of wrist assembly 24. FIG. 6 illustrates swivel mount 34 with pad 48 and plate 90 (FIG. 4) removed. FIG. 6 illustrates the electrical connection between transducers 40 and 42 and electrical wires 280 and 290, respectively. As shown by FIG. 6, swivel mount 34 contains electrical connector 304. Electrical connector 304 receives leads 306 of transducer 40. Leads 306 transmit the electrical signals produced by transducer 40 representing the pressures and transmits the electrical signals to electrical wires 290. Electrical connector 304 further includes an electrical resistor 302 electrically coupled to brass plate 94. Resistor 302 is further electrically coupled to grounded electrical wire 300. As a result, static charge is drained through resistor 302 through electrical connector 304 and through grounded wire 300. Electrical connector 304 permits transducer 40 to be removed and separated from swivel mount 34.

Similarly, transducer 42 includes four electrical leads 310 which are electrically connected to electrical wires 280. In contrast to transducer 40, however, transducer 42 is generally fixed and mounted within swivel mount 34. As shown by FIG. 6, swivel mount 34 electrically connects transducers 40 and 42 to monitor 26 by electrical wires 280 and 290 carried within cables 30 and 32.

III. Monitor 26

Figure 7:
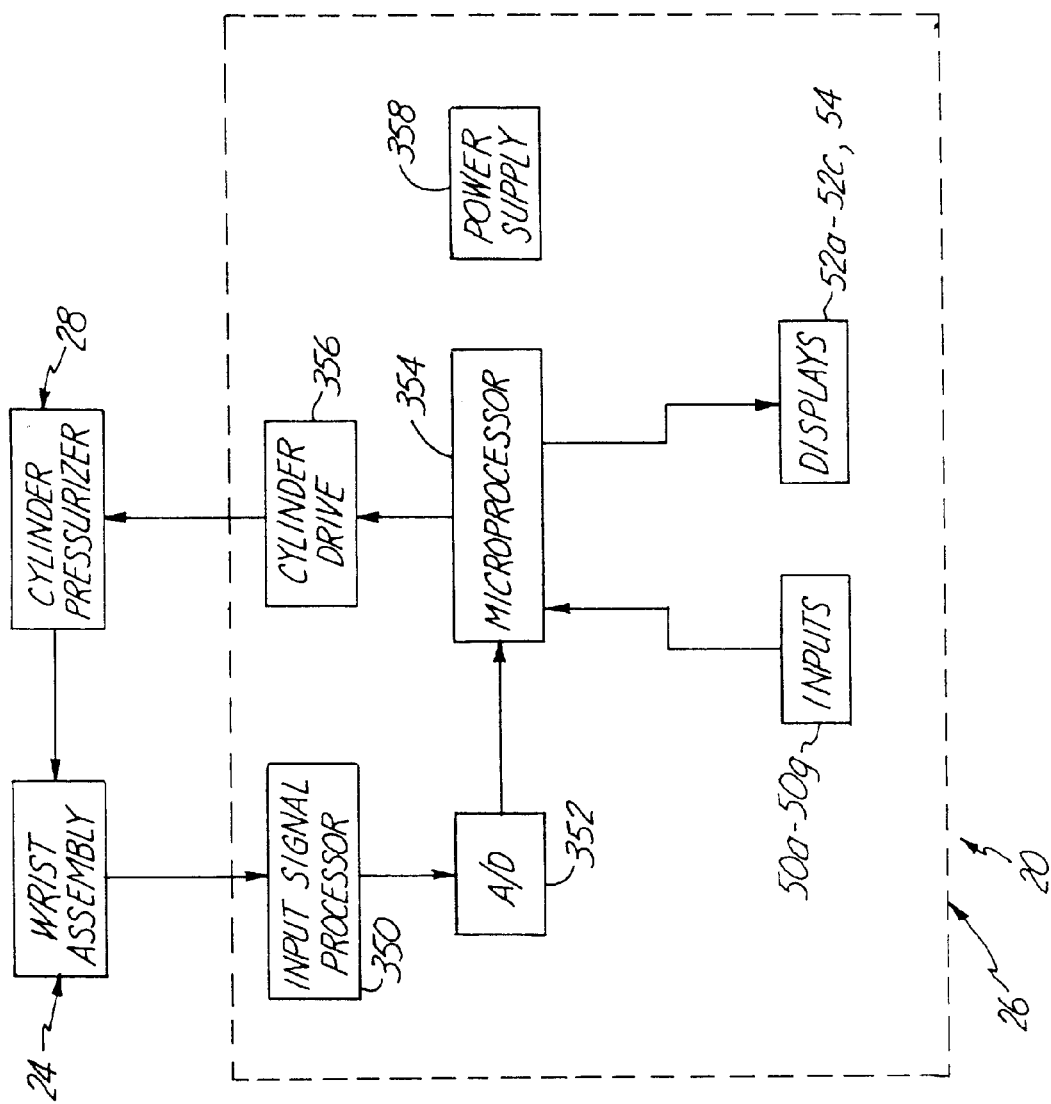
FIG. 7 is an electrical block diagram of the blood pressure monitoring system of FIG. 1.

FIG. 7 shows a block diagram of blood pressure monitoring system 20. As best shown by FIG. 7, monitor 26 further includes input signal processor 350, analog-to-digital converter 352, microprocessor (and associated memory) 354, inputs 50a–50g, cylinder drive 356, displays 52a–52c and 54, and power supply 358. In operation, microprocessor 354 receives inputted signals from inputs 50a–50g. Inputs 50a–50g may also consist of a keyboard or other input mechanisms. Inputs 50a–50g permit microprocessor 354 to perform a calibration.

Microprocessor 354 controls cylinder drive 356 to vary hold down pressure applied by hold down pressure assembly 36 of wrist assembly 24. Hold down pressure is applied to the anatomy of the patient directly above the artery. The hold down pressure applied by hold down pressure assembly 36 on sensor interface assembly 38 is increased over time. As the force or hold down pressure applied by sensor interface assembly 38 increases, the amplitude or relative pressure of the blood pressure pulse also increases until a maximum amplitude results. Once the maximum amplitude or maximum energy transfer results, the amplitude of the blood pressure pulse begins to decrease as the artery begins to flatten out beyond the point of maximum energy transfer.

Transducer 40 of wrist assembly 24 senses the amplitude arid shape of the blood pressure pulses within the underlying artery. Transducer 40 creates electric sensor signals representing the pressures exerted by the sensed blood pressure pulses. The sensor signals are transmitted to input signal processor 350 of monitor 26. Input signal processor 350 processes the sensor signals arid filters any unwanted or undesirable noise and other effects. The sensor signals are then transmitted from input signal processor 350 to analog-to-digital convertor 352. Analog-to-digital convertor 352 converts the sensor signal into digital Form. A digital signal representing the pressures of the sensed blood pressure pulses is sent to microprocessor 354.

Based upon the digital sensor signals representing the sensed pressures and shape of the blood pressure pulses, microprocessor 354 determines wave shape information by measuring amplitude and shape versus time of individual cardiac cycles. The arterial wave shape information is determined by sampling the arterial waves at a rate significantly above heart rate so that a good definition of the arterial pressure wave is measured. From wave shape information and other parameters derived therefrom, microprocessor 354 calculates systolic, diastolic and mean blood pressures.

IV. Method for Locating Sensor Interface Assembly Over Artery

Figure 8:
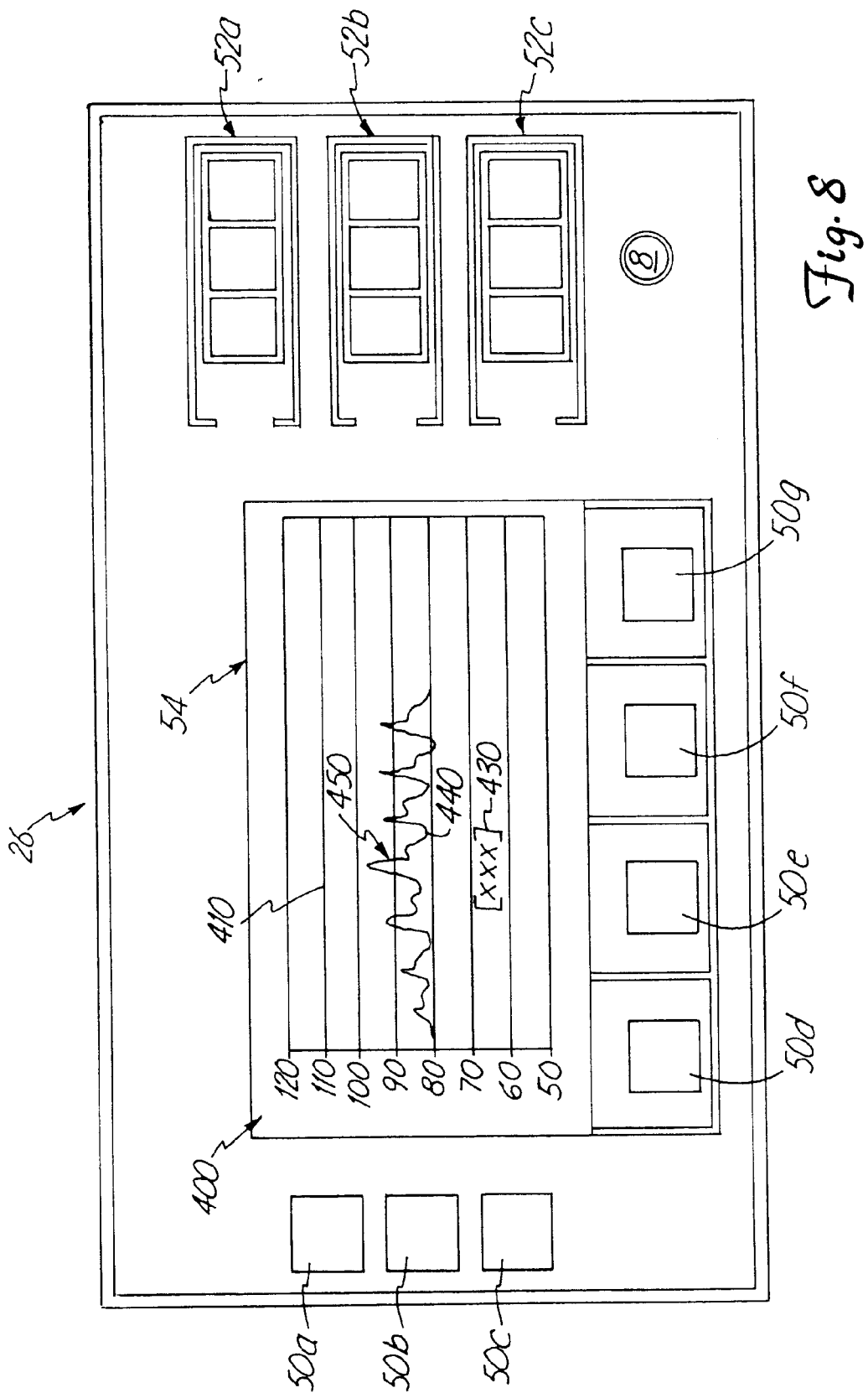
FIG. 8 is a front elevational view of a monitor of the blood pressure monitoring system of FIG. 1.

FIG. 8 illustrates digital displays 52a–52c and display screen 54 of monitor 26 in greater detail. As shown by FIG. 8, display screen 54 further includes pressure scale 400, horizontal guidelines 410 and digital readout 430. Monitor 26 also is used to display blood pressure pulse waveforms so as to guide the operator in positioning and locating sensor interface assembly 38 directly over the underlying artery having a blood pressure pulse so that more accurate blood pressure values may be determined.

To place sensor interface assembly 38 over an underlying artery, sensor interface assembly 38 is located or positioned above a known approximate location of the underlying artery. As sensor interface assembly 38 is positioned over the underlying artery, a constant hold down pressure is applied to sensor interface assembly 38 and to the underlying artery. Preferably, the pressure applied to sensor interface assembly 38 should be as high as possible without the diastolic portion 440 of blood pressure waveforms 450 distorting.

In response to the applied pressure, the underlying artery exhibits a blood pressure pulse waveform for each cardiac cycle. Sensor interface assembly 38 senses or receives the force exerted by the blood pressure pulse as the pulse travels beneath the sensing surface and transmits the pressures through the fluid coupling medium to transducer 40. Transducer 40 in turn senses the changes in pressure and converts the pressures into electrical signals which represent the arterial pressure waveforms. The signals are then transmitted through cables 30 and 32 to monitor 36. Monitor 36 samples the signals preferably at a rate of 128 samples per second. Monitor 36 then visually displays the sampled signals received from transducer 40 and displays the signals representing arterial pressure waveforms on display screen 54. Display screen 54 is preferably indexed so as to provide a vertical scale 400 with horizontal guidelines 410 for displaying pressure. Guidelines 410 permit the maximum pressure amplitude of blood pressure pulse waveforms at the particular location and at a constant hold down pressure to be determined. A representative series of blood pressure pulse waveforms 450 is illustrated on screen 54 in FIG. 8.

To further aid the operator in determining the maximum amplitude of blood pressure pulse waveforms, display screen 54 further includes a digital readout 430 which digitally displays the maximum pressure amplitude exerted by the pulse in response to the hold down pressure applied to the artery. As shown in FIG. 8, the artery exhibits pressures which are in the form of blood pressure pulse waveforms 450 when a constant hold down pressure of 80 mmHg is applied to the underlying artery. Blood pressure pulse waveforms 450 exhibit a maximum amplitude of approximately 18 mmHg.

Once the maximum pressure amplitude exerted by the pulse at a particular hold down pressure at the particular location is determined and noted, sensor interface assembly 38 is repositioned at a second location above the known approximate location of the artery. The same constant hold down pressure is applied to sensor interface assembly 38 and to the underlying artery of wrist 22. The constant hold down pressure applied to the underlying artery is preferably as close as possible to the constant hold down pressure applied at the first location as indicated by display screen 54. This can be done by applying a hold down pressure to sensor interface assembly 38 at a constant force equal to one of guidelines 410.

The maximum pressure amplitude exerted by the pulse in response to the hold down pressure applied to the artery at the second location can be determined from the analog display of the blood pressure waveforms 450 on display screen 54 or the digital readout 430 on display screen 54. The maximum pressure amplitude at the second location is then noted or recorded for comparison with maximum pressure amplitudes at other locations. Typically, sensor interface assembly 38 will be repositioned at a plurality of locations above a known approximate location of the artery while applying a constant hold down pressure to the artery. At each location, the maximum pressure amplitude exerted by the pulse in response to the constant hold down pressure will be displayed on display screen 54 and noted. At each location, the maximum pressure amplitude indicated by display screen 54 is compared with maximum pressure amplitudes exerted by the pulse in response to the constant hold down pressure applied to the artery and indicated by display screen 54 at the plurality of other locations. After the maximum pressure amplitude corresponding to each of the plurality of locations are compared, sensor interface assembly 38 and its sensing surface are positioned at the particular location which corresponds to the location at which the largest of the maximum pressure amplitudes is exerted by the pulse in response to the constant hold down pressure applied to the artery.

V. Method for Determining Blood Pressure Values

Once the sensor is properly positioned over the underlying artery, blood pressure monitoring system 20 determines blood pressure values from the sensed waveform pressure amplitudes sensed by sensor interface assembly 38 and from other parameters derived from the pressure amplitudes using a stored set of coefficients. A pressure amplitude is determined at each sample point.

Blood pressure monitoring system 20 calculates a systolic blood pressure valve (S), a mean blood pressure (M) and a diastolic blood pressure (D) based upon the following formulas:

$$M = F_m(P_1^m, \ldots, P_n^m, \ldots, C_n^m)$$

$$S = F_s(P_1^s, \ldots, C_1^s, \ldots, C_n^s)$$

$$D = F_d(P_1^d, \ldots, P_n^d, C_1^d, \ldots, C_n^d)$$

wherein $F_m$, $F_s$, $F_d$ are linear or non-linear functions, $P_1^m$, $P_1^s$, $P_1^d$, ..., $P_n^m$, $P_n^s$, $P_n^d$ are parameters derived from waveform pressure amplitudes and $C_1^m$, $C_1^s$, $C_1^d$, ..., $C_n^m$, $C_n^s$, $C_n^d$ are coefficients obtained during training processes based upon clinical data.

In particular, blood pressure monitoring system 20 calculates a systolic blood pressure value (S), a mean blood pressure value (M), a diastolic blood pressure value (D) based upon the following formulas:

$$M = C_1^m P_1^m + C_2^m P_2^m + \ldots + C_n^m P_n^m$$

$$S = C_1^s P_1^s + C_2^s P_2^s + \ldots + C_n^s P_n^s$$

$$D = C_1^d P_1^d + C_2^d P_2^d + \ldots + C_n^d P_n^d$$

wherein $P_1^m$, $P_1^s$, $P_1^d$ ... $P_n^m$, $P_n^s$, $P_n^d$ are parameters derived from waveform pressure amplitudes. Such parameters may be calculated from shape characteristics of the waveform or parameters calculated from functions such as curves based upon relationships between particular points of several waveforms. The parameters may be further based upon hold down pressure values and time periods between particular points on the waveforms. The value $C_1^m$, $C_1^s$, $C_1^d$ ... $C_n^m$, $C_n^s$, $C_n^d$ are coefficients obtained during training processes based upon clinical data.

In addition, the pulse rate (PR) may also be determined using the formula:

$$PR = \frac{PR_1 + PR_2 + PR_3 + PR_4}{4}$$

To determine pulse rate, four individual waveforms or beats are sensed and are time averaged to determine pulse rate. Preferably, the waveforms used to determine pulse rates include the waveform having largest maximum pressure amplitude, the two waveforms prior to the waveform having the largest maximum pressure and the waveform succeeding the waveform having the largest maximum pressure. Once the four waveforms are identified, the pulse rate of each waveform is determined. The sum of the pulse rate of the four waveforms is then divided by four to calculate pulse rate PR. The pulse rate (PR) for each waveform is based upon the following formula:

$$PR_N \text{ beats per minute } (N = 1, 2, 3, 4) = \frac{128 \text{ samples/sec}}{\text{No. samples/beat}_N}.$$

Figure 9:
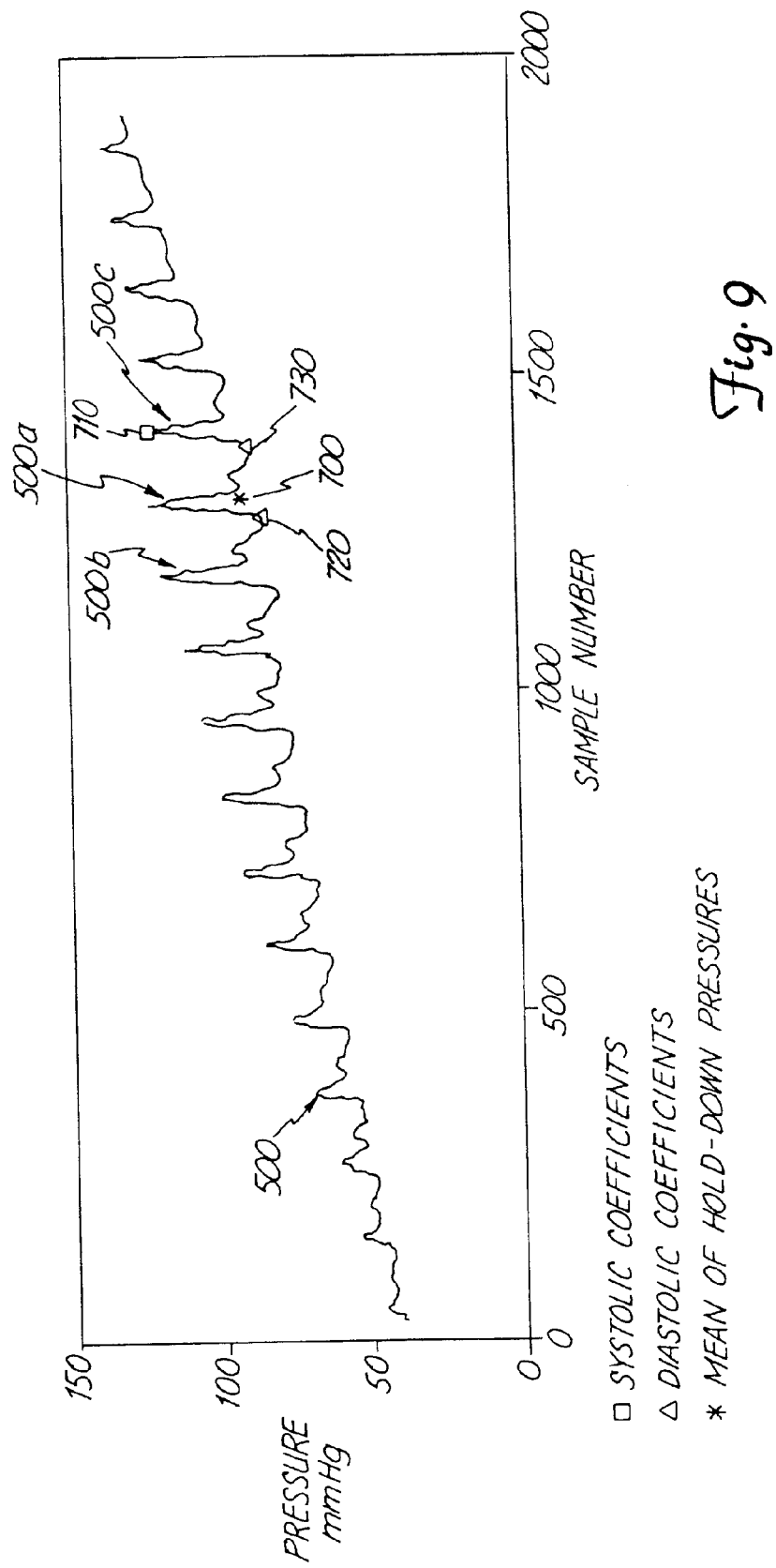
FIG. 9 is a graph illustrating blood pressure waveforms.
Figure 10:
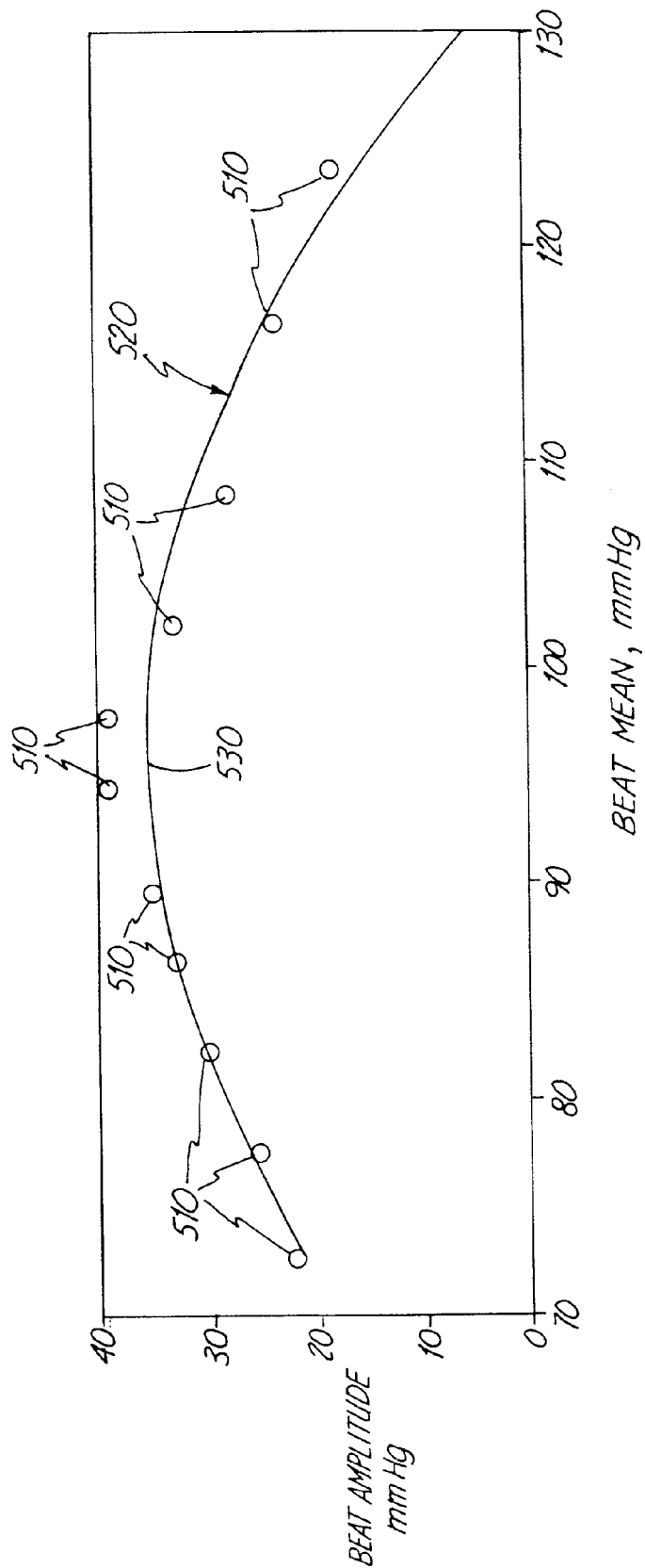
FIG. 10 is a graph illustrating a curve fit from points taken from the waveforms of FIG. 9.

FIGS. 9, 10 and 11 illustrate representative parameters which may be use to calculate blood pressure values. FIG. 9 illustrates a sample series of waveforms exhibited by the underlying artery as a varying pressure is applied over time. The vertical scale indicates pressure in mmHg while the horizontal scale indicates individual sample points at which the blood pressure values exerted by the pulse are measured over time. In the preferred embodiment, transducer 40 produces continuous electrical signals representing waveform pressures which are sampled 128 times per second.

In the preferred embodiment, the hold down pressure applied by hold down pressure assembly 36 to sensor interface assembly 38 (shown in FIG. 1) is swept over a preselected range of increasing hold down pressures. Preferably, the sweep range of hold down pressures is begun at approximately 20 mmHg. The hold down pressure applied by hold down pressure assembly 36 is then steadily increased until two individual waveforms are sensed following the sensed waveform having the largest pressure amplitude. Alternatively, once the waveform having the largest maximum pressure is sensed and identified, successive sweeps may alternatively have a varying hold down pressure applied until a preselected multiple of the mean hold down pressure of the waveform having the largest maximum pressure amplitude is reached. Preferably, each sweep range extends between the initial hold down pressure of 20 mmHg and a final hold down pressure of approximately 150% of the mean hold down pressure of the waveform having the largest maximum pressure amplitude during the previous sweep. In addition, the sweep range may alternatively have an initial hold down pressure of approximately 20 mmHg to a final hold down pressure having a preselected absolute value. Alternatively, the sweep could start at a high pressure and sweep low. As a safety measure, the pressure within pressure chamber (sensed by transducer 42) and interface chamber 210 (sensed by transducer 40) are continually monitored by monitor 26. If the ratio of the pressures within pressure chamber 116 and chamber 210 fall outside of a defined range of limits, an alarm is signaled.

After each hold down pressure sweep, blood pressure monitoring system 20 begins a successive new sweep to calculate new, successive blood pressure values. As a result, blood pressure monitoring system 20 continually measures blood pressure within the underlying artery without causing discomfort to the patient. As can be appreciated, the sweep range of hold down pressure applied by hold down pressure assembly 36 may have various initial and final points. Furthermore, the hold down pressure applied by hold down pressure assembly 36 may alternatively be intermittently varied. For example, the hold down pressure may be increased or decreased in a step-wise fashion.

Based upon sensed and sampled pressure waveform signals or data produced by transducer 40 and sent to monitor 26 during each sweep of hold down pressures, monitor 26 derives preselected parameters for calculating blood pressure values from the derived parameters and a stored set of coefficients. As indicated in FIG. 9, parameters may be derived directly from the absolute waveform pressures which vary as hold down pressure is varied over time. Such parameters may be derived from the shape of the waveforms including a particular waveform's slope, absolute pressure at a selected sample point, a rise time to a selected sample point on a waveform and the hold down pressures corresponding to a particular sample point on a waveform. As can be appreciated, any of a variety of parameters may be derived from the absolute waveform pressures shown in FIG. 9. Parameters may further be based upon particular points or functions of the sample points.

FIG. 10 illustrates an example of how values or parameters of multiple waveforms 500 shown in FIG. 9 may be used to derive additional parameters. FIG. 10 shows several data points 510. Each data point 510 represents a selected waveform taken from the sweep shown in FIG. 9. Curve 520 is derived by fitting points 510 to a preselected function or relationship. Parameters such as the peak 530 are then derived from curve 520. As can be appreciated, various other parameters such as slope may also be derived from curve 520. Parameters derived from curve 520 are ultimately based upon pressure waveforms 500 shown in FIG. 9 which are produced from sensed pressure waveform data or signals from transducer 40. However, because curve 520 is derived using a plurality of waveforms 500, parameters derived from curve 520 represent the overall relationship between the plurality of waveforms 500. In other words, parameters derived from curve 520 represent the way in which the plurality of waveforms 500 (shown in FIG. 9) are related to one another. Data points 510 represent corrected, relative waveform pressures. As can be appreciated, functions such as curves may also be derived using absolute waveform pressure values which are shown in FIG. 9.

A waveform is "corrected" by subtracting the hold down pressure from the absolute pressure of the waveform to produce relative waveform pressures (otherwise known as amplitudes). Correcting a waveform eliminates characteristics of the waveform which result from a continuously increasing hold down pressure being applied to the artery during each waveform or cardiac cycle.

FIG. 11 further illustrates other parameters which may be derived from waveform pressure values as shown in FIG. 9. FIG. 11 illustrates waveform 600 selected from waveforms 500. Waveform 600 is preferably the wavieform having the largest peak or maximum pressure amplitude. Alternatively, waveform 600 may be any of the waveforms 500 (shown in FIG. 9) such as waveforms immediately preceding or succeeding the waveform having the largest maximum pressure. As shown in FIG. 11, waveform 600 is corrected such that the beginning point 602 and an ending point 604 have the same absolute waveform pressure value. As further shown by FIG. 11, waveform 600 is horizontally and vertically scaled to eliminate gain from parameters derived from waveform 600. Preferably, waveform 600 is scaled from zero to twenty-one beginning at beginning point 602 and ending at ending point 604 of waveform 600 on the horizontal b axis. Preferably, waveform 600 is vertically scaled from zero to one beginning at its base and ending at its peak. Because waveform 600 is horizontally and vertically scaled, parameters may be derived from waveform 600 for calculating blood pressure values without the gain of the particular patient affecting the calculated blood pressure value. Gains are caused by the differences between the actual pressure exerted within the artery and the pressures sensed at the surface of the wrist or anatomy which is caused by varying characteristics of the intermediate tissue. Scaling waveform 600 eliminates any gains exhibited by individual patients. By using scaled values to locate corresponding points or waveform pressure amplitudes on waveform 600, points on waveform 600 uniformly correspond to the same points on waveforms exhibited by other patients.

As shown by FIG. 11, various parameters may be derived from scaled, corrected waveform 600. As shown by FIG. 11, such parameters include widths of waveform 600 at selected points along the vertical y axis, ratios of individual waveform pressure amplitudes at selected points along the horizontal b axis and the amplitude of the waveform, the rise time or time elapsed from the start of waveform 600 at point 602 to a selected point along the vertical y axis. In addition, several other parameters may also be derived from waveform 600, such as slope and other shape characteristics.

Once the parameters to be used in calculating blood pressure values are selected, coefficients corresponding to each parameter must be determined. Coefficients represent the relationship between a particular parameter set and the resulting blood pressure value to be determined from a particular parameter set. Coefficients are initially ascertained from clinical tests upon patients having known blood pressure values. Typically, the known blood pressure value is determined using the A-line method which is generally accurate, although difficult to set up, expensive and medically risky. As the blood pressure is determined using, the A-line or other methods, sensor interface assembly 38 is positioned over the underlying artery of the patient. Hold down pressure assembly 36 applies a varying pressure to the artery of the patient having the known blood pressure value. As discussed above, transducer 40 produces sensed pressure waveform signals or data representing arterial pressure waveforms. Monitor 26 receives the produced sensed pressure waveform data and derives preselected parameters from the sensed pressure waveform data. Coefficients are then determined using the derived values of the selected parameters and the known blood pressure value. Each coefficient corresponding to each selected parameter is a function of the known blood pressure values and the derived parameters. Preferably, several patients are clinically tested to ascertain the coefficients. Once obtained, the coefficients are stored for use in non-invasively calculating blood pressure values of other patients without the necessity of using the more time consuming, expensive and risky A-line method and without using the generally more inaccurate conventional blood pressure measuring methods. Each particular coefficient is preferably ascertained so as to be applicable for calculating blood pressure values from the derived waveform parameters of all patients. Alternatively, individualized coefficients may be used to calculate blood pressure values from derived waveform parameters of particular patients falling within a particular age group or other specialized groups. The coefficients are preferably determined for use with the same blood pressure monitoring system as will be used to determine the particular blood pressure value of patients having unknown blood pressure values. However, as can be appreciated, the method of the present invention for ascertaining coefficients as well as the method of the present invention for determining blood pressure values may be used in conjunction with any one of a variety of blood pressure monitoring systems including different sensor assemblies and hold down pressure assemblies.

In addition to illustrating various methods by which parameters may be derived from waveform pressure data, FIGS. 9, 10 and 11 illustrate particular parameters for use in calculating a systolic, a mean and a diastolic blood pressure value of a particular patient during an individual hold down pressure sweep. According to the preferred method of the present invention, hold down pressure assembly 36 applies a sweeping, continuously varying hold down pressure to the underlying artery. Preferably, the hold down pressure applied by hold down pressure assembly 36 during each sweep begins at 20 mmHg and ramps upward over time until at least two waveforms are detected by transducer 40 after the waveform having the largest maximum pressure is identified. Based upon the produced sensed pressure waveform data representing the waveforms as representatively shown by FIG. 9, blood pressure monitoring system 20 calculates systolic, mean and diastolic blood pressure using a stored set of coefficients. Systolic blood pressure (S) is calculated using the formula:

$$S = C_1^s P_1^s + C_2^s P_2^s + C_3^s P_3^s + C_4^s P_4^s + C_5^s P_5^s + C_6^s P_6^s + C_7^s P_7^s + C_8^s P_8^s + C_9^s$$

Coefficients $C_1^s$–$C_9^s$ are stored coefficients ascertained according to the earlier described method of the present invention. $C_9^s$ is an offset value. Parameters $P_1^s$ and $P_2^s$ are derived from relative waveform pressure amplitudes corresponding to scaled values taken from a scaled and corrected beat as represented by waveform 600 in FIG. 11. Preferably, parameter $P_1^s$ is the ratio defined by the waveform pressure amplitude on waveform 600 which corresponds to scale value $b_1$ along the horizontal axis divided by the maximum waveform pressure amplitude or peak (point 606) of waveform 600. Parameter $P_2^s$ preferably is the ratio defined by the waveform pressure amplitude of point 608 on waveform 600 that corresponds to scale value $b_3$ along the horizontal b axis divided by the maximum waveform pressure amplitude or peak (point 606) of waveform 600.

Parameter $P_3^s$ is the rise time or the time elapsed from the start of the waveform to a particular point along waveform 600 corresponding to a particular vertical scale value. Preferably, parameter $P_3^s$ is the elapsed time from the start of waveform 600 to a point 610 on waveform 600 which has a vertical height of approximately 0.18 that of a maximum pressure amplitude or peak (point 606) of waveform 600. This rise time or elapsed time is represented as 612 in FIG. 11.

Parameter $P_4^s$ is the mean pressure of the uncorrected wiveform 500a (shown in FIG. 9) having the highest peak or maximum pressure. Parameter $P_4^s$ is indicated on FIG. 9 by point 700. Parameter $P_5^s$ is the systolic point of the uncorrected pressure waveform immediately following the uncorrected pressure waveform having the largest maximum pressure. Parameter $P_5^s$ is represented by point 710 on FIG. 9.

Parameter $P_6^s$ is a parameter taken from a function such as a curve derived from values of a plurality of waveforms 500 (shown in FIG. 9). Preferably, parameter $P_6^s$ is the peak pressure of curve 520 shown in FIG. 10. The peak is represented by point 530. Curve 520 is preferably generated by fitting the relative waveform pressure amplitude of waveforms 500 (shown in FIG. 9) to the function or mathematical expression of:

AMPLITUDE=$\exp(ax^2+bx+c)$, wherein x=the mean pressure amplitude of each pressure waveform.

Parameter $P_7^s$ is a time value representing a width of waveform 600 (represented by segment 614 between points 616 and 618) which corresponds to a selected percentage of the maximum pressure amplitude or peak (point 606) of waveform 600. The time elapsed between points 616 and 618 is determined by counting the number of samples taken by monitor 26 which lie above points 616 and 618 on waveform 600. Preferably, parameter $P_7^s$ is the width of waveform 600 at a height of about 0.9 A, where A is the maximum waveform pressure amplitude of waveform 600 (point 606).

Parameter $P_8^s$ is the maximum slope of the uncorrected waveform 500c immediately following the waveform 500a having the largest maximum pressure or peak.

The mean blood pressure value (M) is calculated using the formula:

$$M=C_1^m P_1^m+C_2^m P_2^m+C_3^m P_3^m+C_4^m P_4^m+C_5^m$$

Coefficients $C_1^m$–$C_5^m$ are stored coefficients ascertained according to the earlier described method of the present invention. Coefficient $C_5^m$ is an offset. Parameters $P_1^m$ and $P_2^m$ are derived from relative waveform pressure amplitudes corresponding to scaled values taken from the scaled and corrected beat as represented by waveform 600 in FIG. 11. Preferably, parameter $P_1^m$ is the ratio defined by the waveform pressure (point 620) on waveform 600 which corresponds to the scale value $b_9$ along the horizontal axis divided by the maximum waveform pressure amplitude or peak (point 606) of waveform 600. Similarly, parameter $P_2^m$ is the ratio defined by the waveform pressure on waveform 600 which corresponds to scale value $b_{13}$ along the horizontal axis (point 622) divided by the maximum waveform pressure amplitude or peak (point 606) of waveform 600.

Parameter $P_3^m$ is identical to parameter $P_4^s$ used to calculate systolic blood pressure. Parameter $P_4^m$ is identical to parameter $P_6^s$ used to calculate systolic blood pressure.

Diastolic blood pressure values (D) are calculated using the formula:

$$D=C_1^d P_1^d+C_2^d P_2^d+C_3^d P_3^d+C_4^d P_4^d+C_5^d P_5^d+C_6^d P_6^d+C_7^d P_7^d+C_8^d$$

Coefficients $C_1^d$–$C_8^d$ are stored coefficients ascertained according to the earlier described method of the present invention. Coefficient $C_8^d$ is an offset value. Parameter $P_1^d$ is derived from relative waveform pressure corresponding to scaled values taken from a scaled and corrected beat as represented by waveform 600 in FIG. 11. Preferably, parameter $P_1^d$ is a ratio defined by the waveform pressure amplitude on waveform 600 which corresponds to scale value $b_{12}$ along the horizontal axis (point 624) divided by the maximum waveform pressure amplitude or peak (point 606) of waveform 600.

Parameter $P_2^d$ is identical to parameter $P_3^s$ used to calculate the systolic blood pressure. Preferably, parameter $P_3^d$ is the width of segment 626 between points 628 and 630. Preferably points 626 and 628 are points along waveform 600 that are located at a height of 0.875 A, where A is the maximum pressure amplitude (point 606) of waveform 600. The width or time of parameter $P_3^d$ is determined by counting the number of individual waveform pressure amplitude signals or samples generated by transducer 40 and transmitted to monitor 26 which lie above points 626 and 628 on waveform 600. If points 626 and 628 fall between individual waveform pressure amplitude signals or samples, interpolation is used to determine the time width of parameter $P_3^d$.

Parameter $P_4^d$ is identical to parameter $P_4^s$ used to calculate systolic blood pressure. Parameters $P_5^d$ and $P_6^d$ are calculated from absolute waveform pressures as illustrated in FIG. 9. Preferably, parameter $P_5^d$ is the diastolic pressure value of the uncorrected waveform having the largest maximum pressure value. This diastolic value is represented by point 720. Parameter $P_6^d$ is the diastolic pressure value of the uncorrected waveform (waveform 500c) immediately following the waveform (waveform 500a) having the largest maximum pressure amplitude or peak. Parameter $P_6^d$ is represented by point 730 on FIG. 9.

Parameter $P_7^d$ is derived from absolute waveform pressures illustrated in FIG. 9. To derive parameter $P_7^d$, the slopes along the portions of each individual waveform 500 are determined. Parameter $P_7^d$ is the hold down pressure applied to the underlying artery that corresponds to the point on the particular waveform having the maximum slope corrected amplitude. The slope corrected amplitude of a waveform is obtained by multiplying its amplitude with the maximum slope over all waveforms 500 and dividing the result with the slope corresponding to the individual waveform. As can be appreciated, various alternative parameters may also be used to calculate blood pressure values under the method of the present invention.

VI. Conclusion

The present invention enables blood pressures of patients to be continuously and non-invasively determined without the complexity, cost, risks, and inaccuracies associated with the prior methods and apparatuses for determining blood pressure. Wrist assembly 24 securely mounts sensor interface assembly 38 upon wrist 22 of the patient so that patient movement does not alter the optimal location of sensor interface assembly 38 found. The lower pivot point of sensor interface assembly 38 causes pressure applied by the sidewall of assembly 38 to the tissue above the underlying artery to be uniform around the perimeter of the sidewall. As a result, blood pressure monitoring system 20 samples more accurate signals representing blood pressure pulse waveforms. By deriving parameters from the waveform data and using stored coefficients, blood pressure monitoring system consistently and accurately determines blood pressure values.

Although the present invention has been described with reference to preferred embodiments, workers skilled in the art will recognize that changes may be made in form and detail without departing from the spirit and scope of the invention. For example, although the determination of pressure values based upon waveform parameters has been described using linear equations and stored coefficients, other methods using non-linear equations, look-up tables, fuzzy logic and neural networks also can be used in accordance with the present invention.

What is claimed is:

1. A method for determining blood pressure of an artery having a pulse, the method comprising:
   applying a pressure to the artery;
   sensing pressure produced by the artery to produce sensed pressure data representing a pressure waveform for at least one pulse;
   deriving a plurality of parameters related to waveform shape from the sensed pressure data including at least one of the following: (a) rise time of a selected portion of a waveform, (b) applied pressure corresponding to a starting point of a waveform, (c) applied pressure corresponding to an ending point of a waveform, (d) pressure of a waveform at a selected time, (e) a pressure corresponding to a selected point on a waveform, (f) a time value corresponding to a width of a selected portion of a waveform, (g) mean amplitude of a waveform, (h) mean of a curve generated from data taken from a plurality of waveforms; and
   determining a blood pressure value based upon the parameters.

2. The method of claim 1 including:
   selecting a set of data representing a pressure waveform which exhibited a maximum amplitude, wherein at least one of the plurality of parameters is derived from the selected set of data.

3. A non-invasive blood pressure monitoring device, the monitoring device comprising:
   pressure means for applying pressure to the artery so that the artery exhibits pressure data;
   sensing means for sensing the pressure data;
   signal producing means connected to the sensing means for producing output signals corresponding to the sensed pressure data; and
   processing means for receiving the output signals from the signal producing means, for deriving a plurality of parameters related to waveform shape using sensed pressures including at least one parameter other than maximum pressure waveform amplitude and for determining a blood pressure value using the derived parameters.

4. The blood pressure monitoring device of claim 3 herein the sensing means includes:
   a transducer;
   sensor support;
   a flexible diaphragm coupled to the sensor support and having an active portion for transmitting blood pressure pulses of the underlying artery; and
   a fluid coupling medium coupled between the flexible diaphragm and the transducer for transmitting blood pressure pulses within the underlying artery from the flexible diaphragm to the transducer.

5. The blood pressure monitoring device of claim 3 wherein the signal producing means includes:
   an input signal processor for processing data received from the sensing means and for filtering noise; and
   an analog-to-digital converter for converting the signal from the input signal processor into digital form representing pressure of the sensed blood pressure pulses.

6. A method for determining blood pressure of an artery having a pulse, the method comprising:
   sensing pressure data representing pressure waveforms for each of a plurality of pulses produced by the artery while applying a sweeping increasing pressure to the artery;
   deriving parameters related to waveform shape from the sensed pressure data; and
   determining a blood pressure value based upon the parameters.

7. A method for determining blood pressure of an artery having a pulse, the method comprising:
   sensing pressure data produced by the artery during a plurality of pulses while applying an increasing pressure to the artery, the pressure data representing a pressure waveform for each pulse;
   deriving a plurality of parameters related to waveform shape of at least one pressure waveform including at least one parameter other than maximum pressure waveform amplitude from the sensed pressure data; and
   determining a blood pressure value based upon the parameters.

8. A method for determining blood pressure of an artery having a pulse, the method comprising:
   applying a pressure to the artery;
   sensing pressure data produced by the artery representing a pressure waveform for at least one pulse;
   deriving a plurality of waveform shape parameters from the sensed pressure data; and
   determining a blood pressure value based upon the plurality of waveform shape parameters and a stored set of coefficients.

9. The method of claim 8 including:
   selecting a set of data from a plurality of beats, wherein at least one parameter is derived from the selected set of data.

10. A non-invasive blood pressure monitoring device, the monitoring device comprising:
    pressure means for applying a pressure to the artery so that the artery exhibits pressure data representing a pressure waveform for at least one pulse;
    sensing means for sensing the pressure data;
    signal producing means connected to the sensing means for producing output signals corresponding to the sensed pressure data;
    storing means for storing a set of coefficients; and
    processing means for receiving the output signals from the signal producing means, for deriving a plurality of waveform shape parameters using sensed pressures and for determining a blood pressure value using the derived parameters and the stored set of coefficients.

11. A non-invasive blood pressure monitoring device, the monitoring device comprising:
    pressure means for applying a pressure to the artery so that the artery exhibits pressure data representing a pressure waveform for at least one pulse;
    sensing means for sensing the pressure data;
    signal producing means connected to the sensing means for producing output signals corresponding to the sensed pressure data; and
    processing means for receiving the output signals from the signal producing means, for deriving a plurality of parameters related to waveform shape including at least one of the following: (a) rise time of a selected portion of a waveform, (b) applied pressure corresponding to a starting point of a waveform, (c) applied pressure corresponding to an ending point of a waveform, (d) pressure of a waveform at a selected time, (e) a pressure corresponding to a selected point on a waveform, (f) a time value corresponding to a width of a selected portion of a waveform, (g) mean amplitude of a waveform, (h) mean of a curve generated from data taken from a plurality of waveforms.

12. A method for monitoring blood pressure data produced by an artery, the method comprising:

sensing pressure data produced by the artery over time representing a plurality of arterial pressure waveforms;

determining a maximum pressure amplitude for each of the plurality of arterial pressure waveforms from the sensed pressure data;

applying an increasing pressure to the artery until at least one waveform has a maximum pressure amplitude less than a maximum pressure amplitude of a preceding waveform; and determining a blood pressure value based upon shape of a least one of the pressure waveforms.

13. A method for determining blood pressure of an artery, the method comprising:

positioning a sensor having a constant volume fluid filled sensing chamber over the artery;

applying force to the sensor to press the sensor towards the artery;

sensing pressure data produced by the artery by sensing pressure within the constant volume fluid filled chamber to generate pressure waveform data;

deriving waveform shape parameters from the pressure data; and determining a blood pressure value based upon the waveform shape parameters.

14. The method of claim 13 wherein the step of applying varying force to the sensor includes:

applying an increasing force to the sensor.

15. The method of claim 13 wherein the step of applying a varying pressure to the sensor includes:

sweeping the force being applied to the sensor.

16. The method of claim 15 wherein the step of applying a varying force to the sensor includes:

intermittently varying the force applied to the artery.

17. A non-invasive blood pressure measurement system comprising:

a sensor having a constant volume fluid filled sensing chamber configured for being positioned over an underlying artery;

force applying means for applying a force to the sensor to press the sensor against the underlying artery;

sensing means for sensing pressure within the constant volume fluid filled sensing chamber representing pressure data produced by the underlying artery;

signal producing means connected to the sensing means for producing output signals corresponding to the sensed pressures within the constant volume fluid filled sensing chamber;

storing means for storing a set of coefficients; and processing means for receiving the output signals from the signal producing means, for deriving a plurality of waveform shape parameters using the sensed pressures and for determining a blood pressure value using the derived parameters and the stored set of coefficients.

18. The device of claim 17 including:

means for sensing the force applied to the sensor.

19. A non-invasive blood pressure measurement system comprising:

a sensor having a constant volume fluid filled sensing chamber configured for being positioned over an underlying artery;

means for applying force to the sensor to press the sensor against the underlying artery;

sensing means for sensing pressure within the constant volume fluid filled sensing chamber during a plurality of pulses in the underlying artery; and means for deriving a blood pressure value based upon a waveform shape analysis of the sensed pressure representing at least one pressure waveform produced by one of the pulses.

* * * * *

UNITED STATES PATENT AND TRADEMARK OFFICE
CERTIFICATE OF CORRECTION

PATENT NO. : 6,589,185 B1
DATED : July 8, 2003
INVENTOR(S) : G. Kent Archibald et al.

It is certified that error appears in the above-identified patent and that said Letters Patent is hereby corrected as shown below:

Column 3,
Line 31, delete "tonometnc", insert -- tonometric --

Column 12,
Line 62, delete "arid", insert -- and --

Column 13,
Line 1, delete "arid", insert -- and --

Column 17,
Line 9, delete "wavieform", insert -- waveform --

Column 21,
Line 50, delete "herein", insert -- wherein --

Signed and Sealed this

Fourteenth Day of October, 2003

JAMES E. ROGAN
*Director of the United States Patent and Trademark Office*